United States Patent
Atakan et al.

(10) Patent No.: US 10,338,053 B2
(45) Date of Patent: Jul. 2, 2019

(54) CURING-DRYING MODEL AND ITS APPLICATIONS

(71) Applicant: Solidia Technologies, Inc., Piscataway, NJ (US)

(72) Inventors: Vahit Atakan, West Windsor, NJ (US); Xudong Hu, Monroe, NJ (US)

(73) Assignee: Solidia Technologies, Inc., Piscataway, NJ (US)

( * ) Notice: Subject to any disclaimer, the term of this patent is extended or adjusted under 35 U.S.C. 154(b) by 175 days.

(21) Appl. No.: 15/290,328

(22) Filed: Oct. 11, 2016

(65) Prior Publication Data

US 2017/0102373 A1    Apr. 13, 2017

Related U.S. Application Data

(60) Provisional application No. 62/238,912, filed on Oct. 8, 2015.

(51) Int. Cl.
*G01N 33/38* (2006.01)
*B28B 11/24* (2006.01)
*C04B 40/02* (2006.01)

(52) U.S. Cl.
CPC .......... *G01N 33/383* (2013.01); *B28B 11/245* (2013.01); *C04B 40/0231* (2013.01)

(58) Field of Classification Search
None
See application file for complete search history.

(56) References Cited

U.S. PATENT DOCUMENTS

| | | | | |
|---|---|---|---|---|
| 4,069,063 A | * | 1/1978 | Ball | C04B 28/04 106/713 |
| 4,362,679 A | * | 12/1982 | Malinowski | B28B 7/44 264/82 |
| 5,695,811 A | * | 12/1997 | Andersen | B01F 7/00908 427/133 |
| 6,052,964 A | * | 4/2000 | Ferm | E01C 7/147 404/64 |
| 2013/0087075 A1 | * | 4/2013 | Massa | C04B 28/18 106/672 |
| 2014/0013833 A1 | * | 1/2014 | Hosoda | G01N 33/383 73/73 |
| 2015/0246852 A1 | * | 9/2015 | Chen | C04B 28/02 106/682 |

* cited by examiner

*Primary Examiner* — Tuan C Dao
(74) *Attorney, Agent, or Firm* — Dentons US LLP

(57) ABSTRACT

The invention encompasses methods to control the curing of a $CO_2$ Composite Material (CCM) and processes that use such equipment to cure the CCM. The method provides a way to compute the expected water distribution in an uncured porous concrete product based on a set of environmental conditions on.

6 Claims, 32 Drawing Sheets

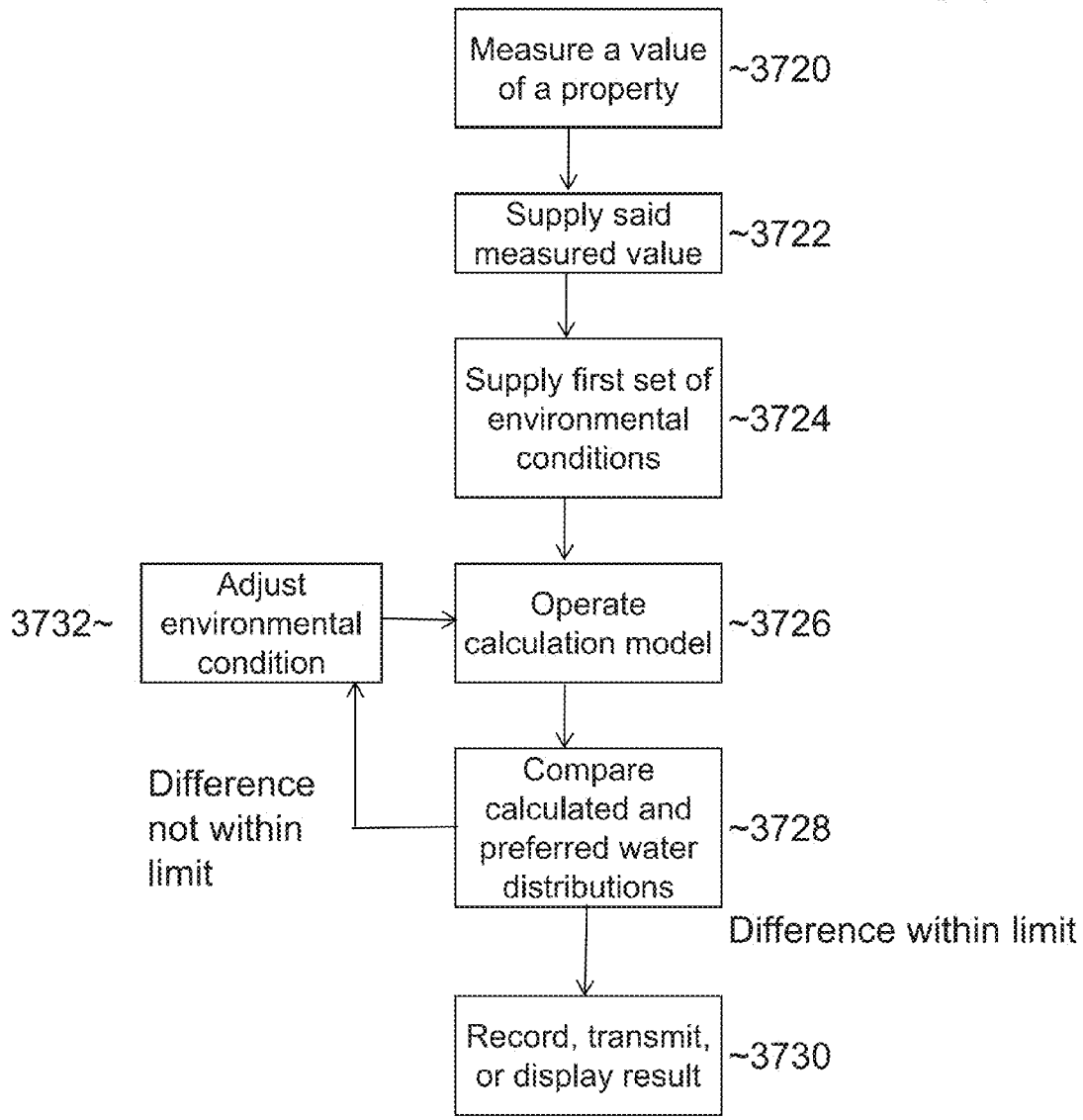

CURING-DRYING MODEL AND ITS APPLICATIONS

CROSS-REFERENCE TO RELATED APPLICATIONS

This application claims priority to and the benefit of U.S. provisional patent application Ser. No. 62/238,912, filed Oct. 8, 2015, which application is incorporated herein by reference in its entirety.

FIELD OF THE INVENTION

The invention relates to systems and methods for curing composite materials in general and particularly to systems and methods that control the water content of the composite as it cures.

BACKGROUND OF THE INVENTION

Curing chambers for many systems of materials are known in the art, including chambers that are configured to handle materials undergo specific chemical reactions. Some of the problems that are associated with conventional curing chambers include their cost, their limitations as regards operating conditions and locations, and the precision with which the curing process may be controlled.

There is a need for curing chambers and methods that provide versatility, precision and reduced costs.

SUMMARY OF THE INVENTION

Porosity Control

This invention relates to the drying/curing model pertaining to carbonation of non-hydraulic cement (e.g., cement that is not cured by the consumption of water in a chemical reaction, but rather is cured by reaction with carbon dioxide, $CO_2$, in any of its forms, such as, by way of example, gaseous $CO_2$, $CO_2$ in the form of carbonic acid, $H_2CO_3$, or in other forms that permit the reaction of $CO_2$ with the non-hydraulic cement material).

This invention interrelates the porosity of the concrete, filler and mortar elements and the time required for carbonation and or drying in the presence of carbon dioxide.

The change in porosity of concrete elements can be manipulated by varying and/or controlling the mixture proportions of ingredients of concretes.

The micro porosity can be manipulated by changing and/or controlling the water to cement ratio of the mixtures and by changing and/or controlling the particle size distribution of cement particles.

These changes are expected to result in different drying curves as well as carbon dioxide diffusion in the systems.

According to one aspect, the invention features a method to control a set of environmental conditions for curing a porous concrete product in a $CO_2$ gas. The method comprises the steps of: measuring a value of a property of an uncured porous concrete product under a first set of environmental conditions; supplying the measured value of the property of the uncured porous concrete product to a calculation model that operates on a general purpose programmable computer; supplying the first set of environmental conditions to the calculation model; operating the calculation model to generate a calculated water distribution in the uncured porous concrete product under the first set of environmental conditions; comparing the calculated water distribution in the porous concrete product to a preferred water distribution to obtain a difference between the subsequent calculated water distribution in the porous concrete product and the preferred water distribution; adjusting one or more of the first set of environmental conditions to generate a subsequent set of adjusted environmental conditions; supplying the subsequent set of adjusted environmental conditions to the calculation model; operating the calculation model to generate a subsequent calculated water distribution in the porous concrete product under the subsequent set of adjusted environmental conditions; comparing the subsequent calculated water distribution in the porous concrete product to the preferred water distribution; in the event that the difference between the subsequent calculated water distribution in the porous concrete product and the preferred water distribution is smaller than a predetermined limit, performing at least one of recording as a result the set of adjusted environmental conditions that produce a calculated water distribution in the porous concrete product that differs from the preferred water distribution by less than the predetermined limit, transmitting the result to a data handling system, or displaying the result to a user; and in the event that the difference between the subsequent calculated water distribution in the porous concrete product and the preferred water distribution is not smaller than the predetermined limit, repeating the steps of adjusting one or more environmental conditions, supplying, operating, and comparing until a difference between a further calculated water distribution in the porous concrete product and the preferred water distribution is smaller than the predetermined limit, and then performing at least one of recording as a result the set of adjusted environmental conditions that produce a calculated water distribution in the porous concrete product that differs from the preferred water distribution by less than the predetermined limit, transmitting the result to a data handling system, or displaying the result to a user.

In one embodiment, the property of an uncured porous concrete product is at least one of a water permeability, a porosity, a residual saturation, a sample dimension, a drying side and a critical Relative Humidity.

In another embodiment, the set of preferred environmental conditions includes at least one of a mass transfer coefficient, a relative humidity profile, a temperature profile and a pressure.

In an additional embodiment, the temperature profile comprises a temperature in the range of 30° C. to 90° C.

In yet another embodiment, the water distribution in the porous concrete product is a first surface saturation level in the range of 0.05 to 0.8.

In still another embodiment, the water distribution in the porous concrete product is a second surface saturation level in the range of 0.05 to 0.8.

In a further embodiment, the method further comprises the step of applying the subsequent set of environmental conditions to a curing apparatus in a curing process.

The invention encompasses equipment used to condition a recirculating gas stream in order to cure a $CO_2$ Composite Material (CCM) and processes that use such equipment to cure the CCM. The gas conditioning equipment allows for a process that controls, reduces or eliminates the rate-limiting steps associated with water removal during the curing of a composite material. The equipment may include, but will not be limited to, control over the temperature, relative humidity, flow rate, pressure, and carbon dioxide concentration within the system; which includes the conditioning equipment, any vessel containing the CCM, and the material itself. Flow rate control can be used as a means to achieve uniformity in both gas velocity and composition.

According to one aspect, the invention features a curing system for curing a material which requires $CO_2$ as a curing reagent. The material does not cure in the absence of $CO_2$. The material does not consume water as a reagent. The curing system comprises a curing chamber configured to contain a material that consumes $CO_2$ as a reactant (or reagent) and that does not cure in the absence of $CO_2$. The curing chamber has at least one port configured to allow the material to be introduced into the curing chamber and to be removed from the curing chamber, and has at least one closure for the port, the closure configured to provide an atmospheric seal when closed so as to prevent (or to limit to an innocuous level) contamination of a gas present in the curing chamber by gas outside the curing chamber; a source of carbon dioxide configured to provide gaseous carbon dioxide to the curing chamber by way of a gas entry port in the curing chamber, the source of carbon dioxide having at least one flow regulation device configured to control a flow rate of the gaseous carbon dioxide into the curing chamber; a gas flow subsystem configured to circulate the gas through the curing chamber during a time period when the material that consumes $CO_2$ as a reactant is being cured; a temperature control subsystem configured to control a temperature of the gas within the chamber; a humidity control subsystem configured to control a humidity in the gas within the chamber to increase or decrease humidity; and at least one controller in communication with at least one of the source of carbon dioxide, the gas flow subsystem, the temperature control subsystem, and the humidity control subsystem; and at least one controller configured to control independently during a time period when the material that consumes $CO_2$ as a reactant is being cured at least a respective one of the flow rate of the gaseous carbon dioxide, the circulation of the gas through the curing chamber, the temperature of the gas, and the humidity in the gas.

According to one aspect, the invention features a curing system for curing a material to be cured by reaction with carbon dioxide. The curing system comprises a gas conditioning system and a curing chamber connected together by a gas delivery tube and a gas recovery tube, the curing chamber configured to contain the material to be cured by reaction with carbon dioxide; the gas conditioning system including a source of carbon dioxide, a gas flow subsystem, a temperature control subsystem, a humidity control subsystem and a subsystem for controlling the curing process parameters; the subsystem for controlling the curing process parameters comprising a controller having a microprocessor configured to operate under the control of a set of instructions recorded on a first machine-readable medium so as to control a curing process of the material to be cured by reaction with carbon dioxide.

According to one aspect, the invention features a controller. The controller comprises a microprocessor configured to operate under the control of a set of instructions recorded on a first machine-readable medium, the microprocessor when operating under the set of instructions performing the following steps: controlling the operation of at least one of a source of carbon dioxide, a gas flow subsystem, a temperature control subsystem, and a humidity control subsystem; instituting a flow of a process gas containing carbon dioxide so as to contact a material to be cured by reaction with the carbon dioxide in the process gas; monitoring at least one parameter selected from the group of parameters consisting of an elapsed time from the instituting of the flow, a carbon dioxide concentration, a relative humidity, a flow rate, a temperature, and a pressure of the process gas as the process gas is being provided; and performing at least one of recording at least one of the monitored parameters, transmitting the at least one of the monitored parameters to a data handling system, or to displaying the at least one of the monitored parameters to a user.

In one embodiment, the microprocessor when operating under the set of instructions performs the step of receiving a start command from an external source.

In another embodiment, the microprocessor when operating under the set of instructions performs the step of determining whether a curing chamber is properly loaded.

In yet another embodiment, the microprocessor when operating under the set of instructions performs the step of determining whether a curing chamber is properly closed.

In still another embodiment, the microprocessor when operating under the set of instructions performs the step of determining a state of cure of the material to be cured by reaction with the carbon dioxide.

In a further embodiment, the microprocessor when operating under the set of instructions performs the step of monitoring at least one parameter selected from the group of parameters consisting of a carbon dioxide concentration, a relative humidity, a flow rate, a temperature, a pressure, and a flow duration of the process gas as the process gas is removed from contact with the material to be cured by reaction with the carbon dioxide.

In yet a further embodiment, the microprocessor when operating under the set of instructions performs the step of monitoring at least one parameter selected from the group of parameters consisting of a carbon dioxide concentration, a relative humidity, a flow rate, a temperature, and a pressure at one or more locations within a curing chamber.

In an additional embodiment, the microprocessor when operating under the set of instructions performs the step of receiving input from a user representing one or more process parameters constituting a step of a process to be performed.

In one more embodiment, the microprocessor when operating under the set of instructions performs the step of recording in a non-volatile machine readable medium the input from the user as a step in a process recipe.

In still a further embodiment, the microprocessor when operating under the set of instructions performs the step of retrieving at least one step of a process recipe recorded on a non-volatile machine readable medium.

In one embodiment, the first machine readable medium and the non-volatile machine readable medium are the same medium.

According to another aspect, the invention relates to a gas flow subsystem. The gas flow subsystem comprises at least one of a valve, a flow regulator, a mass flow controller, a blower, and a gas delivery structure; the gas flow subsystem configured to provide a process gas comprising carbon dioxide as a reagent in fluid contact with a material to be cured by reaction with the carbon dioxide.

In one embodiment, the gas flow subsystem is compatible with water vapor in addition to the process gas comprising carbon dioxide as a reagent.

In another embodiment, the gas flow subsystem is compatible with air in addition to the process gas comprising carbon dioxide as a reagent.

In yet another embodiment, the gas delivery structure is embedded in the material to be cured by reaction with the carbon dioxide.

In still another embodiment, the gas delivery structure is a gas permeable layer placed adjacent the material to be cured by reaction with the carbon dioxide.

In a further embodiment, the gas flow subsystem further comprises a communication port configured to receive control signals from a controller.

In yet a further embodiment, the gas flow subsystem further comprises a communication port configured to communicate to a controller a signal encoding at least one of a carbon dioxide concentration, a relative humidity, a flow rate, a temperature, and a pressure of the process gas.

In an additional embodiment, the gas flow subsystem further comprises a gas recovery tubulation.

In one more embodiment, the gas flow subsystem further comprises a communication port configured to communicate to a controller a signal encoding at least one of a carbon dioxide concentration, a relative humidity, a flow rate, a temperature, and a pressure of a gas present in the gas recovery tubulation.

According to another aspect, the invention relates to a temperature control subsystem. The temperature control subsystem, comprises at least a selected one of a heater and a cooler, the temperature control subsystem configured to control a temperature of a process gas containing carbon dioxide so as to cause the process gas to attain a desired temperature prior to coming into contact with a material to be cured by reaction with the carbon dioxide in the process gas.

In one embodiment, the temperature control subsystem further comprises a sensor configured to measure a gas temperature.

In another embodiment, the sensor is a thermocouple.

In yet another embodiment, the temperature control subsystem further comprises a sensor configured to measure a relative humidity.

In still another embodiment, the temperature control subsystem further comprises a communication port configured to communicate a signal representing at least one of a temperature value and a relative humidity value to a controller.

In a further embodiment, the temperature control subsystem further comprises a communication port configured to receive a control signal from a controller.

In yet a further embodiment, the temperature control subsystem is configured to employ the control signal to cause the at least a selected one of the heater and the cooler to operate.

According to another aspect, the invention relates to a humidity control subsystem. The humidity control subsystem, comprises at least a selected one of a water vapor source and a water vapor removal apparatus, the humidity control subsystem configured to control a humidity of a process gas containing carbon dioxide so as to cause the process gas to attain a desired humidity prior to coming into contact with a material to be cured by reaction with the carbon dioxide in the process gas.

In one embodiment, the water vapor source comprises a source of water, a valve and a spray head.

In another embodiment, the water vapor source comprises a steam generator.

In yet another embodiment, the steam generator comprises a submersible heater.

In another embodiment, the water vapor source comprises a bubbler containing water through which a gas may be bubbled.

In yet another embodiment, the water vapor removal apparatus is a chiller.

In still another embodiment, the water vapor removal apparatus is a condenser.

In yet another embodiment, the water vapor removal apparatus is a heat exchanger.

In a further embodiment, the humidity control subsystem further comprises a humidity sensor configured to measure a relative humidity of the process gas.

In yet a further embodiment, the humidity control subsystem further comprises a communication port configured to communicate a signal representing the relative humidity value to a controller.

In an additional embodiment, the humidity control subsystem further comprises a communication port configured to receive a control signal from a controller.

In one more embodiment, the humidity control subsystem is configured to employ the control signal to cause the at least a selected one of the water vapor source and the water vapor removal apparatus to operate.

According to one aspect, the invention features a curing chamber. The curing chamber comprises an enclosure defining an enclosed volume, the enclosure comprises a wall configured to contain a material to be cured by reaction with carbon dioxide in a process gas, the enclosure comprises a closeable opening configured to allow the material to be cured to be introduced into the enclosure; an inlet port configured to allow the process gas containing carbon dioxide to enter the enclosure; and an outlet port configured to allow the process gas to exit the enclosure.

In one embodiment, the curing chamber further comprises a plenum situated within the enclosure, the plenum configured to provide the process gas by way of one or more locations at which the process gas can be injected into the enclosure.

In another embodiment, the plenum is configured to control at least one of a flow velocity, a flow direction, and a flow pattern of the process gas in the enclosure.

In yet another embodiment, the plenum is configured to direct a flow of the process gas to at least one of an outside of the material to be cured and to an internal passage defined in the material to be cured.

In still another embodiment, the inlet port is configured to control at least one of a flow velocity, a flow direction, and a flow pattern of the process gas in the enclosure.

In a further embodiment, the outlet port is configured to control at least one of a flow velocity, a flow direction, and a flow pattern of the process gas in the enclosure.

In yet a further embodiment, the wall is a flexible wall.

In an additional embodiment, the flexible wall is fabricated from a selected one of plastic, Mylar® and latex.

In one more embodiment, the flexible wall includes a coating configured to retain thermal energy.

In still a further embodiment, the wall includes an aperture covered with a material that is transparent in a spectral region of interest.

In one more embodiment, at least one sensor is present within the enclosure, the at least one sensor configured to provide data about at least one of a property of the process gas and an operating condition within the enclosure.

According to another aspect, the invention relates to a cast-in-place method. The cast-in-place method comprises the steps of: preparing a location at which a material to be cured by reaction with carbon dioxide in a process gas is to be situated; placing a process gas delivery structure and the material to be cured by reaction with carbon dioxide in the prepared location; and providing the process gas to the material to be cured by way of the process gas delivery structure for a time period sufficiently long to effect a cure of the material to be cured.

In one embodiment, the process gas delivery structure remains with the material to be cured after the curing process is completed.

In another embodiment, the cast-in-place method further comprises the step of covering the process gas delivery structure and the material to be cured by reaction with carbon dioxide after they are placed in the prepared location.

In yet another embodiment, the step of providing the process gas includes controlling a parameter of the process gas selected from the group of parameters consisting of an elapsed time from the instituting of the flow, a carbon dioxide concentration, a relative humidity, a flow rate, a temperature, and a pressure of the process gas as the process gas is being provided.

In still another embodiment, the cast-in-place method further comprises the step of controlling an amount of water present in the material to be cured by reaction with carbon dioxide.

In a further embodiment, the step of controlling an amount of water present in the material to be cured comprises a selected one of removing water from the material or adding water to the material.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

Figure 32A:
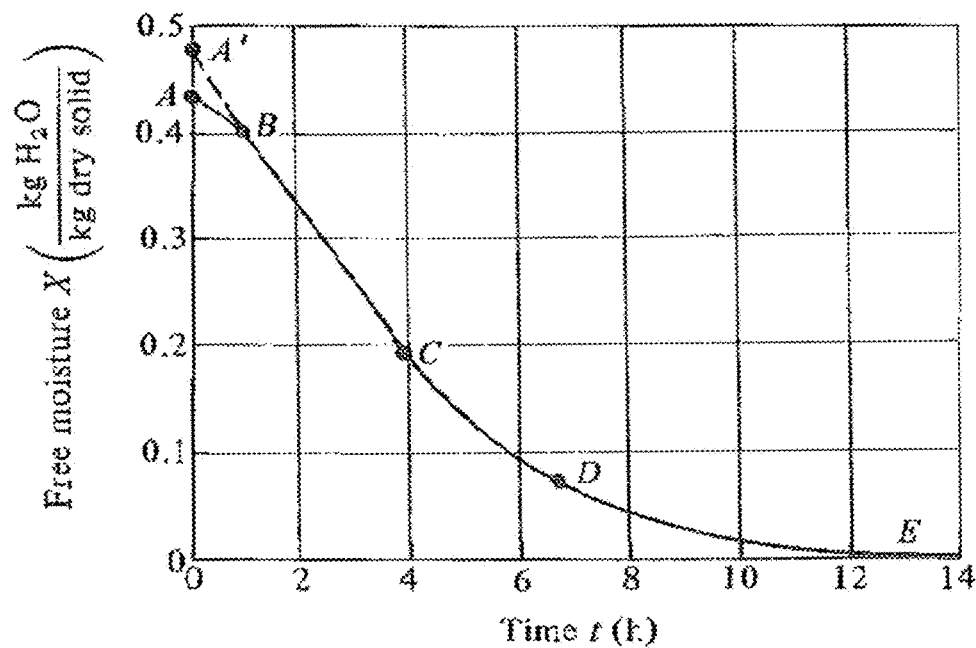
FIG. 32A is a graph illustrating free moisture X vs. time for a typical drying curve, in which AB is a transient period, BC is a constant rate period in which capillary flow occurs, CD is a first falling rate period, in which a transition from capillary flow to water vapor diffusion occurs, and DE is a second falling rate period in which water moves by water vapor diffusion.

As will become apparent, the method to control a set of environmental conditions for curing a porous concrete product in a $CO_2$ gas that is claimed can be used at any point along the curve in FIG. 32A, and can also be used repeatedly at a plurality of points along the curve in FIG. 32A in a repeated or iterative manner. For example one could use points B, C, D and E as intended points in the curing process. One could also take intermediate points along the curve as points to be attained in the process. One can define a preferred water distribution in the uncured product. By using the computational methods described herein, one can compute a water distribution in the uncured product and can compare that water distribution to the preferred water distribution. The environmental conditions can be changed or varied in the computation to find a set of environmental conditions that produces a water distribution that differs from the preferred conditions by less than a predetermined amount, or limit. When environmental conditions are defined that result in a water distribution sufficiently close to the preferred water distribution, those conditions can be applied as part of the curing process. As the process proceeds, repeated or iterated application of the computational method can be used to reach the next intended point in the curing process.

Figure 32B:
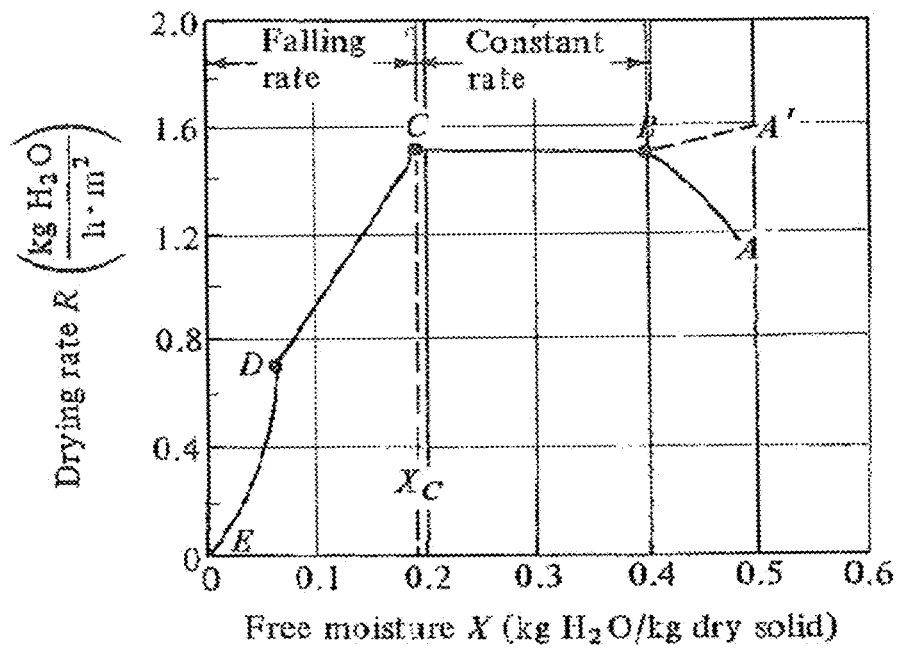

FIG. 32B is a graph illustrating drying rate R vs. time for a typical drying curve, in which periods AB, BC, CD and DE are the same as explained with regard to FIG. 32A.

Figure 33:
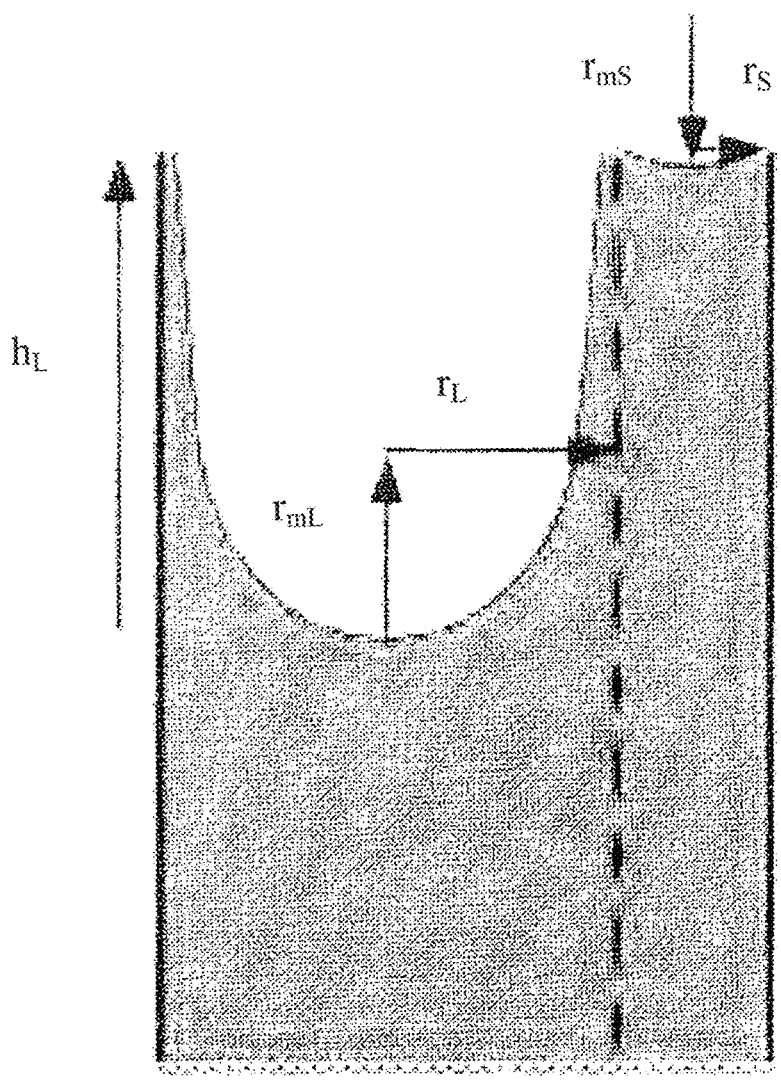

FIG. 33 is a schematic diagram illustrating that the Darcy Flux to the Surface is equal to the Evaporation Rate.

Figure 34:
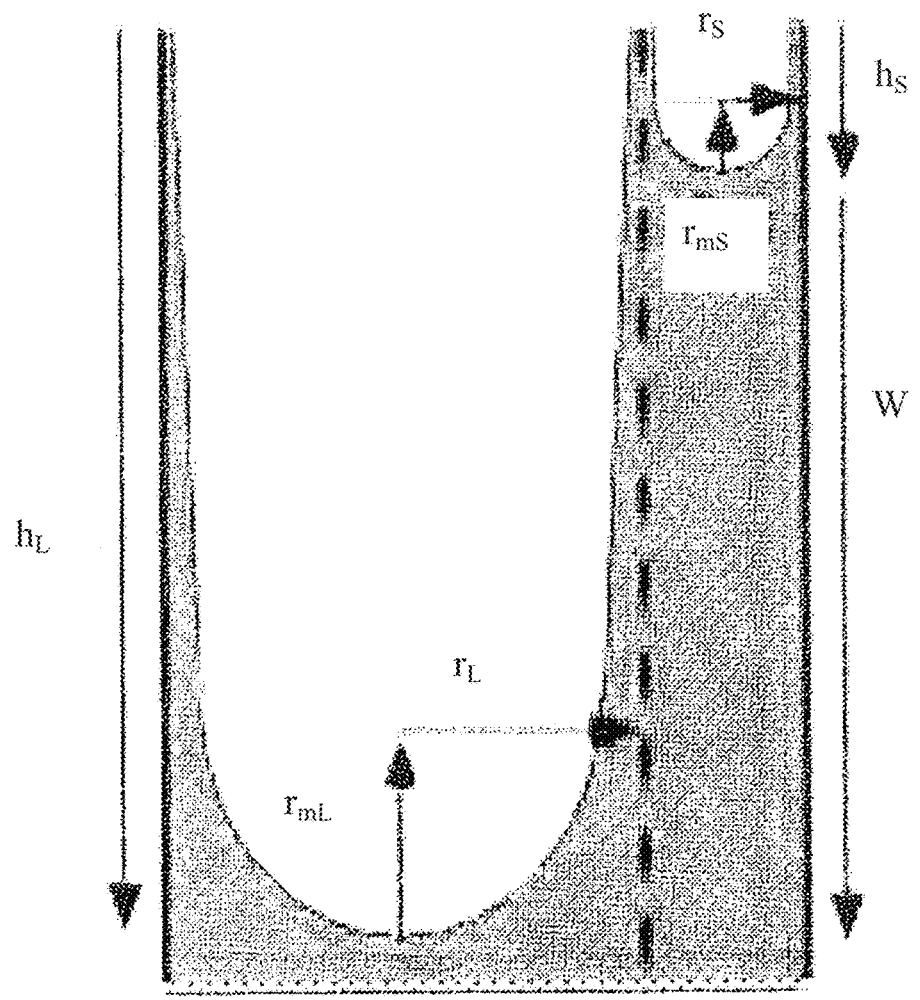

FIG. 34 is a schematic diagram that illustrates the flow of water from the larger pore to the smaller pore after evaporation, as compared to FIG. 33.

Figure 35:
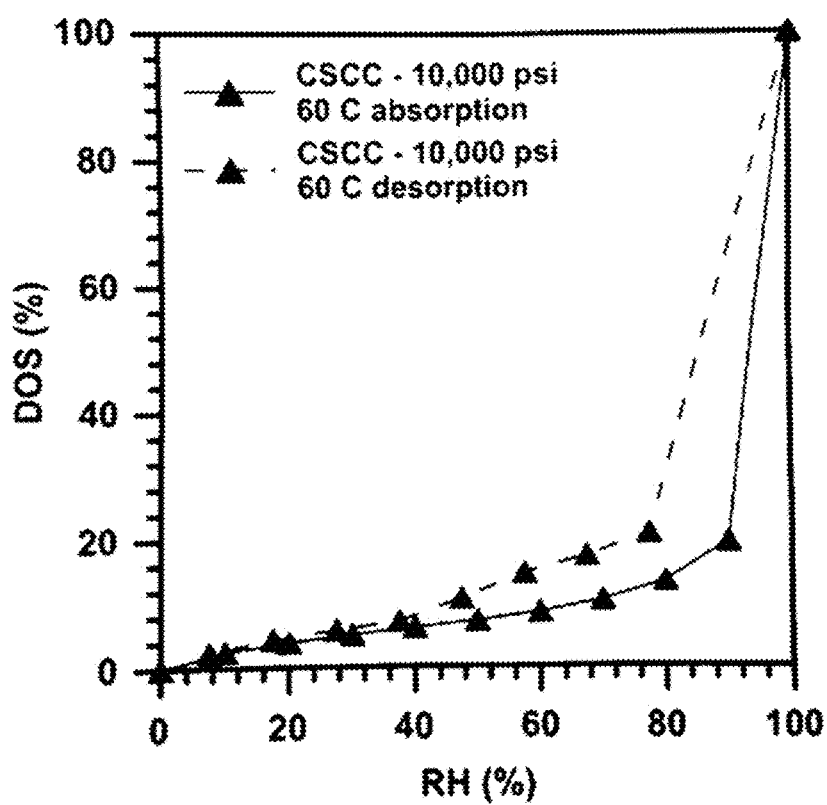

FIG. 35 is a graph of degree of saturation vs. relative humidity (RH).

Figure 36:
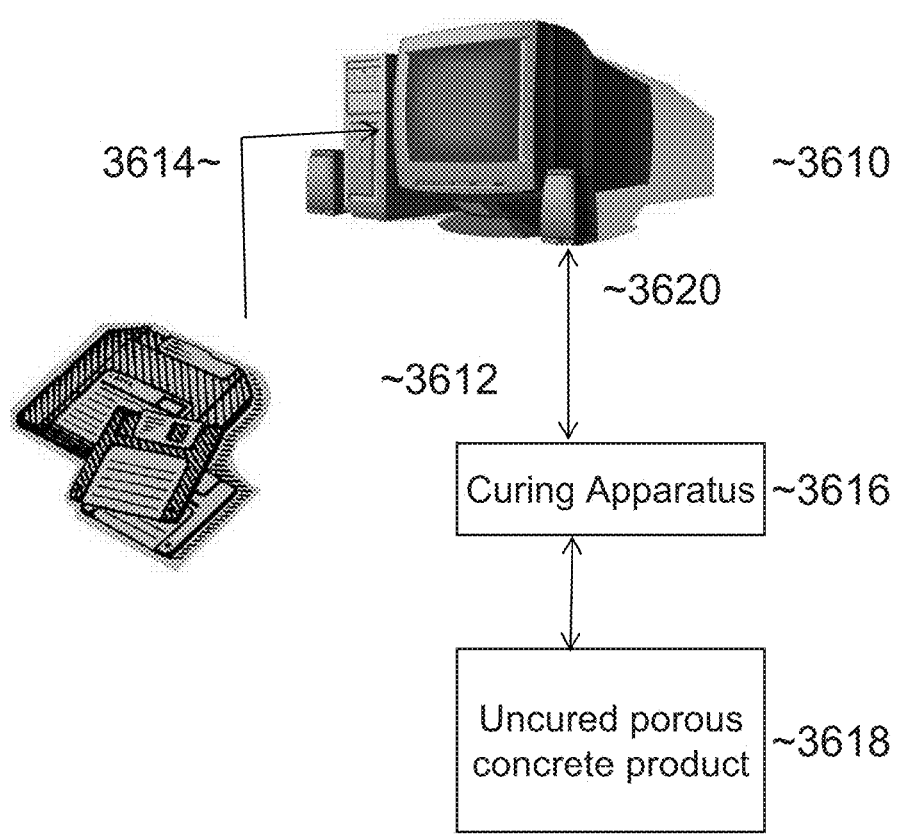

FIG. 36 is a diagram illustrating the relationships among a general purpose programmable computer upon which a calculation model operates, a curing apparatus, and an uncured porous concrete product. The calculation model that operates on the general purpose programmable computer is recorded on a machine readable medium as a nonvolatile set of instructions.

FIG. 37 is a flow diagram illustrating the method of calculating the water distribution in an uncured porous concrete product that is carried out with the general purpose programmable computer upon which a calculation model operates.

DETAILED DESCRIPTION

Solidia Drying-Curing Mathematical Model

This invention relates to the drying/curing model pertaining to carbonation of non-hydraulic cement (e.g., cement that is not cured by the consumption of water in a chemical reaction, but rather is cured by reaction with carbon dioxide, $CO_2$, in any of its forms, such as, by way of example, gaseous $CO_2$, $CO_2$ in the form of carbonic acid, $H_2CO_3$, or in other forms that permit the reaction of $CO_2$ with the non-hydraulic cement material).

Water removal in the drying process has two regimes, constant drying rate period (i.e., capillary flow) followed by a falling rate time period (i.e., water vapor diffusion).

Larger pores are opened up wide during capillary flow but not so for small pores, $CO_2$ can penetrate the small distance in a matter of minutes in the small pores in the size of a few hundred micrometers. In addition, capillary flow is a much faster process than the water vapor diffusion process. The drying/curing model developed is exclusively focused on constant drying rate period in this work.

A mathematical drying/curing model is described that is able to predict the uniformity of the carbonation sample. The model is based on one atmospheric pressure curing pressure, but it can be extended to a higher or lower curing pressure.

Two stages of curing processes are identified in order to have a uniform curing, preconditioning in the air followed by a high concentration of $CO_2$ carbonation curing.

The drying/curing model applies to the constant drying time period where the capillarity of water remains, or technically speaking, water percolation remains intact.

Several sample parameters are identified in the development of the drying model. These parameters are saturated water permeability, residual saturation, sample porosity, sample dimensions, water sorptivity, and so on.

Saturated water permeability is approximated by conducting water sorptivity measurement and D50 of pore size in the green body or slightly carbonated sample measured by an Mercury Intrusion Porosimetry (MIP) technique.

The sample pore pressure, water saturation distribution, water permeability distribution and evaporation rate can be predicted using the model by chosen a set of preconditioning temperature, relative humidity, and flow conditions during preconditioning.

A specific example of roof tile preconditioning using this model is illustrated in detail, demonstrating what the sample and chamber specific inputs are and what the model outputs are.

The drying model water saturation distribution in the sample can be experimentally validated.

If the drying model is tied to the cement power reactivity data, the curing pathway (carbonation degree) can be predicted.

If the total curing time is given, an optimal sample preconditioning temperature and relative humidity can be selected by using the model.

This invention relates to the drying/curing model pertaining to carbonation of non-hydraulic cement (e.g., cement that is not cured by the consumption of water in a chemical reaction, but rather is cured by reaction with carbon dioxide, $CO_2$, in any of its forms, such as, by way of example, gaseous $CO_2$, $CO_2$ in the form of carbonic acid, $H_2CO_3$, or in other forms that permit the reaction of $CO_2$ with the non-hydraulic cement material).

The constant drying rate behavior is believed to be based on capillarity, and the falling drying rate is believed to be based on the loss of capillarity (and is explained by percolation theory). The model is believed to provide a fast and predictable analysis of the behavior of the modeled systems. The model can be used in several different ways. Examples are now given.

One can use the model to predict the curing behavior (or the curing path or trajectory) for a given set of input parameters based on the materials in the mix to be cured, temperature, pressure (generally taken as one atmosphere, but this can be varied as will be explained), relative humidity and other parameters.

The parameters include:

Equipment parameters include Surface temperature: T (Chamber T), Evaporation constant (mass transfer coefficient): $k_E$ (drying curve), Chamber RH, Initial RH: RH0, Final RH: RH1, and Rate of change of RH: RHrate.

Sample parameters include Porosity $\phi$, Volume of the sample V, Sample thickness (if evaporating from one side) or half-thickness (if evaporating from both sides) L, Liquid permeability of saturated body: $k_0$ (sorptivity and MIP), Residual saturation $S_L$ (normally between 0.05 and 0.15), and Critical RH (saturation curve).

Given a desired curing regime, one can predict the composition and particle size distributions of the input materials that will allow curing under the desired curing regime.

One can use the output data taken from a curing process in a curing apparatus by comparing the data to values computed from the model so as to predict the curing behavior and to allow active control of the curing process.

One can use the output taken from a curing process in a curing apparatus and the model to predict when a given product will be sufficiently cured to terminate the curing process.

The model output (also referred to as "deliverables") can be such information as the time sequence that the curing process is expected to follow (e.g., the state of the process at any discrete time interval after the process has been started). The model can be operated as a time slice or discrete time interval computation, using a time interval that is short enough to capture the variations in the process that are of interest, and long enough that the computational burden and amount of data generated are not onerous.

The drying-curing model is tied to the cement reactivity data, which in turn is related to the chemical compositions of particles and the particle size distribution of the cement constituents.

In the calculation scheme outlined, the total pressure is assumed to be one atmosphere (e.g., a pressure of 14.7 pounds per square inch). However, it is recognized that one can model systems at lower pressures (in which the evaporation of water would be expected to be higher, but the pressure of $CO_2$ might have to be increased to provide the same partial pressure of $CO_2$ so as to maintain a reaction rate, other things being equal). Temperature variations have been explicitly modeled.

Darcy flow is a phenomenon that occurs between pores in a solid. The Darcy flow is given by the equation $$V = \frac{q}{A} = -\frac{k}{\mu}\frac{\Delta P}{\Delta L}$$

where V is flow velocity, q is volumetric flow rate, A is flow cross section, $\mu$ is viscosity, L is flow depth, P is pore pressure across the flow depth, and k is water permeability.

FIG. 32A is a graph illustrating free moisture X vs. time for a typical drying curve, in which AB is a transient period, BC is a constant rate period in which capillary flow occurs, CD is a first falling rate period, in which a transition from capillary flow to water vapor diffusion occurs, and DE is a second falling rate period in which water moves by water vapor diffusion.

FIG. 32B is a graph illustrating drying rate R vs. time for a typical drying curve, in which periods AB, BC, CD and DE are the same as explained with regard to FIG. 32A.

FIG. 33 is a schematic diagram illustrating that the Darcy flux to the surface is equal to the evaporation rate. The large pore capillary pressure is given by $$P_L = -\frac{2\gamma \cos\theta}{r_L}.$$

The small pore capillary pressure is given by $$P_S = -\frac{2\gamma \cos\theta}{r_S}.$$

The water flux J is given by $$J = -\frac{k}{\mu}\frac{P_S - P_L}{h_L} = V_E.$$

FIG. 34 is a schematic diagram that illustrates the flow of water from the larger pore to the smaller pore after evaporation, as compared to FIG. 33. The pressure gradient driving flow from the large pore to the small pore is based on the Laplace equation, and can be expressed as $$\frac{P_S - P_L}{W} = -\frac{2\gamma}{W}\left(\frac{1}{r_S} - \frac{1}{r_L}\right).$$

One can think of the volume in a large pore (e.g., one on the left in FIG. 33 and FIG. 34) as being effectively infinite, while the volume in the smaller pores (on the right in FIG. 33 and FIG. 34) is effectively finite.

FIG. 35 is a graph of degree of saturation vs. relative humidity (RH). In FIG. 35 (slide 13), the vertical axis is labeled DOS (%), which stands for Degree of Saturation (in percent). One can control the DOS by controlling the Relative Humidity (RH).

The evaporation rate, $V_E$, ($m^3$ of liquid/($m^2 \cdot s$) is observed to be proportional to the difference in vapor pressure between the surface, $P_{surface}$ (unit Pa) and the surroundings (ambient), $P_{amb}$ (unit, Pa):

$$V_E = K_E(P_{surface} - P_{amb})$$

where $K_E$ (m/(Pa·s) is the mass transfer coefficient, and the pressures are in Pascal. Note that $P_{surface}$ is the saturation pressure at the sample surface which approximates the saturation pressure at the wet bulb temperature in the constant rate drying time period which is applied in the calculation. One can calculate $K_E$ and h from the drying curve.

The following partial differentiation equation is solved to obtain the water distribution of the sample over time (Olivier Coussy, "Mechanics and Physics of Porous Solids", (Wiley, Chichester, U K, 2010) p 213).

$$\phi\frac{\partial S_L}{\partial t} = \frac{\partial}{\partial z}\left[\frac{k[S_N]}{\mu}\frac{\partial P}{\partial z}\right]$$

In this equation, t (second) is time and z (m) is the drying distance coordinate perpendicular to the surface, $S_L$ is the saturation, $\mu$ is the viscosity (Pa·s), P is pore pressure (Pa), $k[S_N]$ is water permeability ($m^2$) at an infinitely small slice of the sample.

The above equation assumes that there is no shrinkage and evaporation occurs only at one outer surface. It is a continuity (or, conservation of mass) equation.

To solve the equation, one needs to establish the relationship between $S_L$ (saturation) and P (pore pressure) as well as the relationship between $k[S_N]$ permeability of sample and P (pore pressure).

Pore pressure is related to saturation in the following equation based on the work of Baroghel-Bouny et al. (Cement Concrete Research, 29(1999), 1225-1238).

$$P = a(S_L^{-b} - 1)^{1 - 1/b}$$

where parameter a is given by the following equation $$a = \left[\frac{RT}{V_m}\ln[RH_{crit}]\right] / \left[\sqrt{\frac{1-S_r^2}{S_r}}\right]$$

n which R is gas constant J/mol·K, T is temperature K, Vm is water molar volume, m³/mol, RHcrit is critical relative humidity, Sr is residual saturation and b≈2.

Next, we need to establish the relationship between $k[S_N]$ permeability of sample and P (pore pressure).

$$k[S_N]=k_0 kr$$

where $K_O$ is initial saturated permeability, m², and Kr is relative permeability, between 0 and 1.

Kr, relative permeability, is described by van Genuchten equation (M. Th. Van Genuchten, "A closed-form equation for predicting the hydraulic conductivity of unsaturated soils", Soil Sci. Soc. Am. J. 44(1980), 892-898)

$$Kr = S_L^{0.5}\left(1-(1-S_L^b)^{\frac{1}{b}}\right)^2$$

where b=2 for cement and concrete materials in van-Genuchten equation (Baroghel-Bouny et al., Cement Concrete Research, 29(1999), 1225-1238), $S_L$ and pore pressure (P) relationship is described in the above section. So, the permeability of $k[S_N]$ is related to pore pressure P.

With properly defined initial and boundary conditions, we are able to solve the partial differential equation described above and output the calculated data of pore pressure versus time evaporation rate versus time, and permeability versus time.

The parameter Sr (residual saturation) is a parameter that one can select as an input parameter (e.g., how dry one wants the cured material to be at the curing end-point). Capillarity is discontinued or the model program terminates calculation when the surface saturation drops down to Sr.

An Exemplary Model

In FIG. 36, a general purpose programmable computer 3610 is provided with a set of instructions (a calculation model) that, when operating on the general purpose programmable computer 3610, perform a calculation of an expected water distribution within an uncured porous concrete product. The set of instructions is recorded on a non-volatile machine readable medium 3612, such as a floppy disk, that can be in communication (via arrow 3614) with the general purpose programmable computer 3610. The general purpose programmable computer 3610 is in bidirectional communication via arrow 6320 with a curing apparatus 3616 (such as are described in various ones of FIGS. 1-31) which itself contains an uncured porous concrete product 3618.

FIG. 37 is a flow diagram illustrating the method of calculating the water distribution in an uncured porous concrete product that is carried out with the general purpose programmable computer upon which a calculation model operates.

In FIG. 37, at step 3720 the process performs the step of measuring a value of a property of an uncured porous concrete product under a first set of environmental conditions.

At step 3722 the process performs the step of supplying the measured value of the property of the uncured porous concrete product to a calculation model that operates on a general purpose programmable computer.

At step 3724 the process performs the step of supplying the first set of environmental conditions to the calculation model.

At step 3726 the process performs the step of operating the calculation model to generate a calculated water distribution in the uncured porous concrete product under the first set of environmental conditions.

At step 3728 the process performs the step of comparing the calculated water distribution in the porous concrete product to a preferred water distribution to obtain a difference between the calculated water distribution in the porous concrete product and the preferred water distribution.

In the event that the difference between the calculated water distribution in the porous concrete product and the preferred water distribution is smaller than a predetermined limit, the process proceeds to step 3730 which performs at least one of recording as a result the set of adjusted environmental conditions that produce a calculated water distribution in the porous concrete product that differs from the preferred water distribution by less than the predetermined limit, transmitting the result to a data handling system, or displaying the result to a user.

In the event that the difference between the calculated water distribution in the porous concrete product and the preferred water distribution is not smaller than the predetermined limit the process proceeds to step 3732.

In step 3732, the process performs the step of adjusting one or more of the first set of environmental conditions to generate a subsequent set of adjusted environmental conditions.

The process than proceeds through steps 3726 and 3728 using the subsequent set of adjusted environmental conditions.

In the event that the difference between the subsequent calculated water distribution in the porous concrete product and the preferred water distribution is not smaller than the predetermined limit, the process repeats steps 3732, 3726, and 3728 until the difference between the subsequent calculated water distribution in the porous concrete product and the preferred water distribution is smaller than the predetermined limit, at which point the process performs step 3730.

Parameters Specifications in the Drying Model and the Partial Differential Equation Sample Parameter Specifications:

Water permeability is the parameter that quantifies how fast the water can move within the sample in liquid form. The higher the water permeability, the easier and faster the water can move in the sample. Darcy's law describes liquid flow in purely viscous flow in consolidated porous media.

Porosity is a measurement of void space and is the fraction of the volume of voids over a total volume in a porous media; it is between 0 and 1, or percentage 0% to 100%.

Residual saturation is defined as the fraction of the pore space that contains water. As drying proceeds, the pore pressure becomes increasingly negative and the saturation drops from initial 1 toward 0. Water permeability is zero when the sample reaches residual saturation.

Sample dimensions include the sample length, width and height.

The drying side is (the side (or the sides) that are exposed to the environment in which the drying proceeds.

Critical RH may be deduced from the saturation curve (desorption only) of the material at which the saturation drops to residual saturation.

The saturation curve is obtained by placing a small piece of material in a controlled RH device for an extended time period until there is no mass change occurs in the specimen. It measures the equilibrium moisture content at specified RH. If the material contains less moisture than its equilibrium value, it will adsorb water until it reaches its equilibrium value. If the material contains more moisture than its equilibrium value in contact with a gas of a given humidity, it will dry until it reaches equilibrium value.

Environmental Parameter Specifications

Mass transfer coefficient is the parameter that quantifies how fast the material of interest is moved away from the surface of the sample. In our case, the material of interest is water vapor. This parameter depends on the flow on the sample surface. If the sample has more than one exposed surfaces, then the mass transfer coefficient needs to be measured for each surface exposed.

A relative humidity profile is defined as how much the gas on the sample surface is saturated with water vapor as a function of time. This is not a single number in the model but it is a profile which includes ramp up rate, dwell time and any other changes with time.

A temperature profile is the temperature on the sample surface as a function of time. Like relative humidity, this is not a single number in the model but it is a profile including the ramp up rate, dwell time or any other changes with time.

A Wet bulb temperature profile is measured using the wet bulb method. When a liquid evaporates, it absorbs energy, so the temperature of the surface decreases. As a result, the surface of the drying body drops to the wet bulb temperature, which depends on the temperature and relative humidity into which evaporation, occurs.

Output of the Model

Saturation level ($S_L$) rep[resents the degree of saturation of a surface of interest in the sample given as a function of time. When the surface of interest is fully saturated with water, the corresponding $S_L$ value is equal to 1, when it is fully dry, the corresponding $S_L$ value is equal to 0.

Pore pressure (Pa) is the difference between the pressure in the liquid and the pressure in the surrounding atmosphere. The pore pressure is zero for a flat pool of liquid, but pore pressure is negative if the liquid has a concave meniscus. When the pore pressure is negative, it means that there is suction in the liquid, so it pulls the solid matrix of the porous media into compression and causes shrinkage during drying.

Carbonation curing is a curing process in which the concrete made of calcium silicate containing cement is reacted with $CO_2$ gas in the presence of water to form a solid hardened body. Carbonation curing can be done at any temperature and pressure that is industrially practical.

The invention relates to methods of processing or "curing" composite materials by means of controlling the atmospheric conditions in and around the material in a precise manner; as well as the equipment involved in doing so.

$CO_2$ Composite Material

The present invention relies in part on the use of materials that undergo curing in the presence of carbon dioxide ($CO_2$) that can be supplied in gaseous form and that is believed to be active in hydrated form (e.g., as a water soluble carbonate derived from $H_2CO_3$). The cured materials that result from such processes will be referred to collectively herein as "$CO_2$ Composite Material" ("CCM") or "$CO_2$ Composite Materials" ("CCMs"). The chemistry and preparation of various kinds of $CO_2$ Composite Material has been described in various patent documents, including U.S. Patent Application Publication No. 20140127450 A1, published May 8, 2014 and U.S. Patent Application Publication No. 20140127458 A1, published May 8, 2014.

The $CO_2$ Composite Materials may exhibit aesthetic visual patterns as well as display compressive strength, flexural strength and water absorption similar to that of the corresponding natural materials. The $CO_2$ Composite Materials can be produced using the efficient gas-assisted hydrothermal liquid phase sintering (HLPS) process at low cost and with much improved energy consumption and carbon footprint. In fact, in preferred embodiments of the process, $CO_2$ is consumed as a reactive species resulting in net sequestration of $CO_2$.

The $CO_2$ Composite Materials can be made to display various patterns, textures and other characteristics, such as visual patterns of various colors. In addition, the $CO_2$ Composite Materials exhibit compressive strength, flexural strength and water absorption properties similar to conventional concrete. The $CO_2$ Composite Materials can be cured to a point where they are ready for use in time intervals (such as hours) that are often considerably reduced from the times required to cure conventional concrete (such as days to weeks). Furthermore, the $CO_2$ Composite Materials can be produced using the energy-efficient HLPS process and can be manufactured at low cost and with favorable environmental impact. For example in preferred embodiments of the invention, $CO_2$ is used as a reactive species resulting in sequestration of $CO_2$ in the produced $CO_2$ Composite Materials with in a carbon footprint unmatched by any existing production technology. The HLPS process is thermodynamically driven by the free energy of the chemical reaction(s) and reduction of surface energy (area) caused by crystal growth. The kinetics of the HLPS process proceed at a reasonable rate at low temperature because a solution (aqueous or nonaqueous) is used to transport reactive species instead of using a high melting point fluid or high temperature solid-state medium.

Discussions of various aspects of HLPS can be found in U.S. Pat. No. 8,114,367, U.S. Pub. No. US 2009/0143211 (application Ser. No. 12/271,566), U.S. Pub. No. US 2011/0104469 (application Ser. No. 12/984,299), U.S. Pub. No. 20090142578 (application Ser. No. 12/271,513), WO 2009/102360 (PCT/US2008/083606), WO 2011/053598 (PCT/US2010/054146), WO 2011/090967 (PCT/US2011/021623), U.S. application Ser. No. 13/411,218 filed Mar. 2, 2012 (Riman et al.), U.S. application Ser. No. 13/491,098 filed Jun. 7, 2012 (Riman et al), U.S. Provisional Patent Application No. 61/708,423 filed Oct. 1, 2012, and U.S. Provisional Patent Application Nos. 61/709,435, 61/709,453, 61/709,461, and 61/709,476, all filed Oct. 4, 2012, each of which is expressly incorporated herein by reference in its entirety for all purposes.

The terms "rate-limiting step" or "rate limiting steps" refer to one or more steps that are restricting or controlling the time a carbonation reaction takes.

Flow is the movement of gas described as a velocity and/or volume, using velocity in fps (feet per second) or volumetrically as cfm (cubic feet per minute).

The term "temperature" or "temperature range" represents one or more of the overall internal system temperature, a gas temperature, and a sample temperature.

The term "relative humidity" represents the ratio of the partial pressure of water vapor in a gas in the system to the saturated vapor pressure of water in that gas at a certain temperature, which may vary throughout the system.

The term "$CO_2$ concentration" represents the amount of $CO_2$ in a system divided by the total volume of gas in that system, expressed as a percentage.

The invention contemplates a process that maximizes the carbonation rate of a composite material by controlling the drying rate of that material. The process can include a carbonation duration is between 0 and 1,000 hours. The process can include a $CO_2$ Composite Material that has a permeability in the range of 0% and 100%. The process can include a $CO_2$ Composite Material that has a carbonation depth of the CCM in the range of 0 and 36 inches. The process can include a $CO_2$ Composite Material wherein the amount of water removed from the CCM is equal to between 0% and 99% of the CCM mass.

The invention encompasses the equipment used to condition a recirculating gas stream in order to cure a CCM and processes that use such equipment to cure the CCM. The gas conditioning equipment allows for a process that controls, reduces or eliminates the rate-limiting steps associated with water removal during the curing of a composite material. The equipment may include, but will not be limited to, control over the temperature, relative humidity, flow rate, pressure, and carbon dioxide concentration within the system; which includes the conditioning equipment, any vessel containing the CCM, and the material itself. Flow rate control can be used as a means to achieve uniformity in both gas velocity and composition.

The equipment can comprise various subsystems. The subsystems can include a curing chamber, a source of carbon dioxide, a gas flow subsystem, a temperature control subsystem, a humidity control subsystem, and a controller in communication with at least one of the source of carbon dioxide, the gas flow subsystem, the temperature control subsystem, and the humidity control subsystem; and at least one controller configured to control independently during a time period when the material that consumes $CO_2$ as a reactant is being cured at least a respective one of the flow rate of the gaseous carbon dioxide, the circulation of the gas through the curing chamber, the temperature of the gas, and the humidity in the gas.

Curing Chambers

Figure 1:
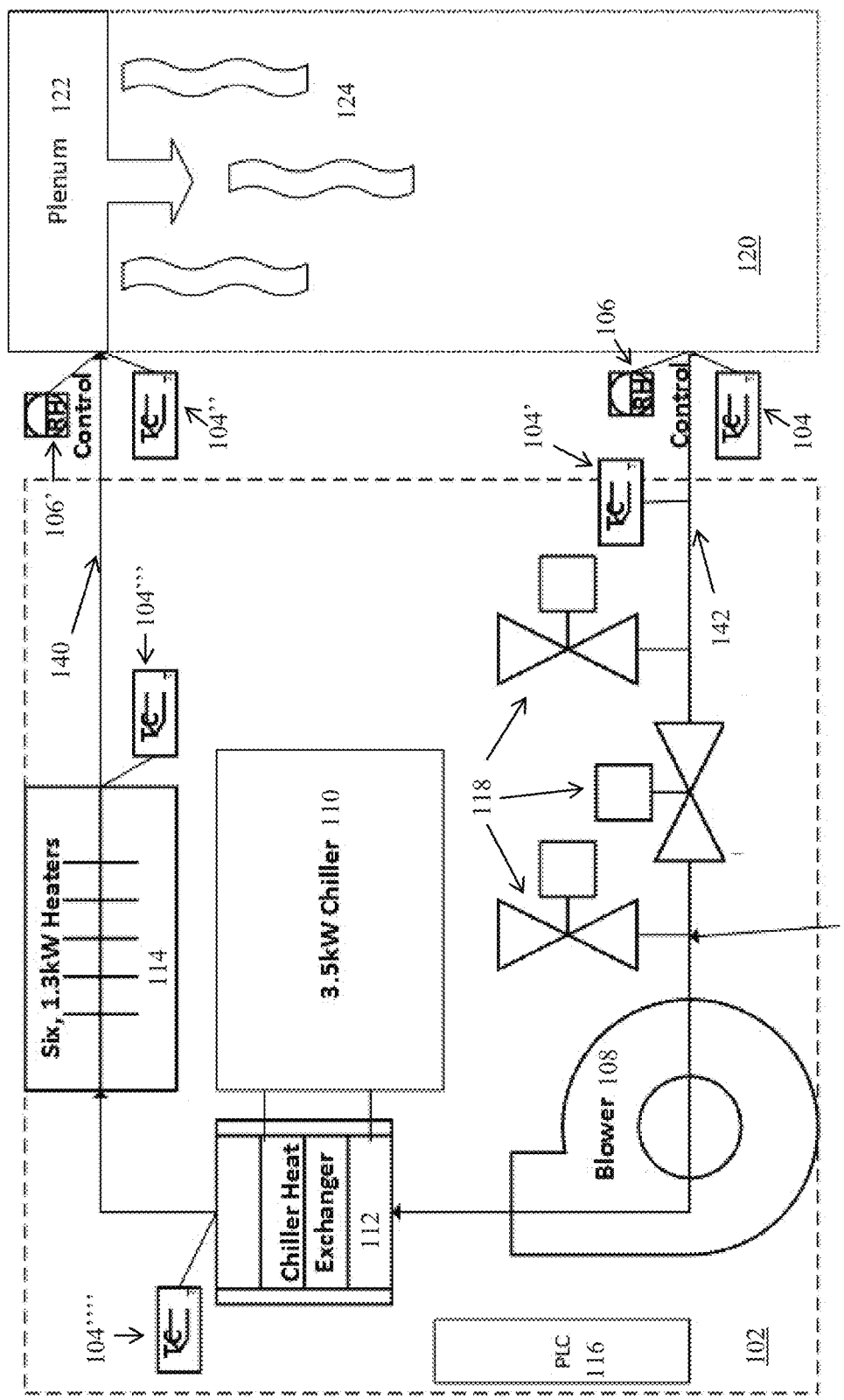
FIG. 1 is a schematic diagram of an embodiment of a curing system for use with $CO_2$ Composite Material.
Figure 2:
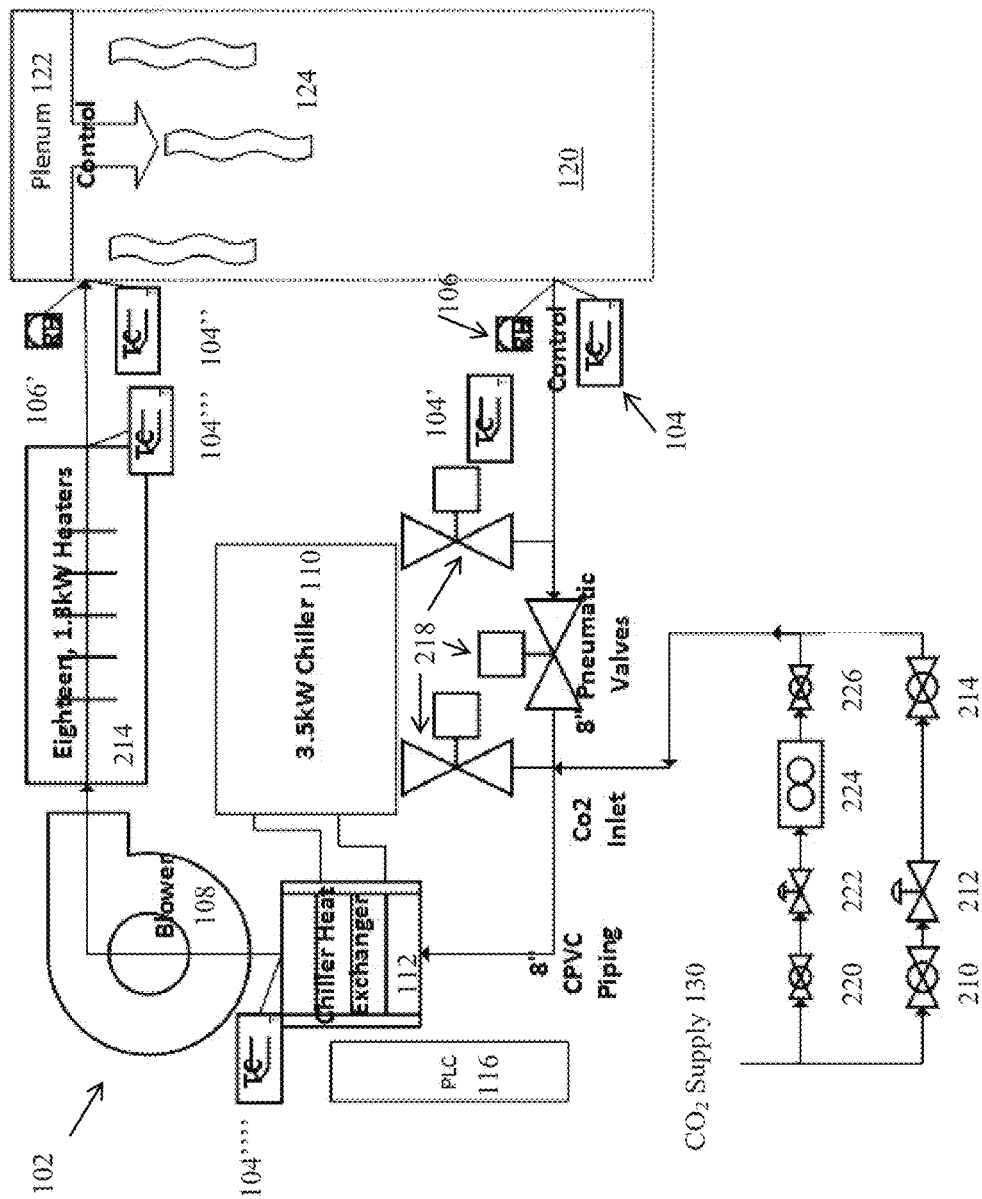
FIG. 2 is a schematic diagram of an embodiment of an alternate curing system for use with $CO_2$ Composite Material.

Various types of curing chambers and apparatus can be employed for curing CCMs. Some curing chambers and apparatus may be provided in permanent or semi-permanent facilities, while others may be used for a time (e.g., temporary installation) and some may be used once (e.g., curing a CCM in place, for example at some out-of-doors location, such as curing a CCM for form a slab for a walkway, a driveway, a road, a landing strip, or a support slab for a structure). FIG. 1 and FIG. 2 are schematic diagrams of embodiments of a curing system for use with $CO_2$ Composite Material.

In some embodiments, the chamber or enclosure itself may be designed for one or a few repetitions of a curing process, or may be designed to last for an indefinitely long number of repetitions of a curing process. In some embodiments, the relative cost of the chamber as compared to the value of the product being cured will serve as a guide as to the materials and methods of construction of the chamber or enclosure.

Source of Carbon Dioxide

Carbon dioxide may be provided from any convenient source that can supply sufficient gas quantities at high enough purity. In some embodiments, the source of carbon dioxide is gas generated from liquid carbon dioxide. In some embodiments, the source of carbon dioxide is gas provided in the form of gas in a high pressure cylinder. In some embodiments, the source of carbon dioxide is effluent from a combustion system that is processed to provide a supply of purified carbon dioxide.

Gas Flow Subsystem

In some embodiments there is provided a gas flow subsystem for providing the necessary gases (e.g., $CO_2$, water vapor, air, and possibly other gases) that are useful for curing a CCM. The gas flow system includes as components one or more of valves, flow regulators, mass flow controllers, and blowers that are suitable for causing gas flows at desired flow rates (e.g., suitable mass per unit of time), desired pressures, and desired compositions (e.g., ratios or proportions of carbon dioxide to water to air and possibly other gases). The curing chamber can further include structures that control the flow rates and flow directions in the curing chamber, as well as the physical locations of gas inlets and outlets.

Temperature Control Subsystem

In some embodiments there is provided a temperature control subsystem that allows the provision of gas having desired gas temperature. The temperature control subsystem can be useful to control reaction rates as a function of temperature, as well as operational parameters such as relative humidity that have a temperature dependence. The temperature control system can comprise one or more heaters, one or more coolers, one or more sensors configured to measure a gas temperature at a location, and a communication port configured to communicate with a controller. In some embodiments, the communication is unidirectional, for example communication in which the controller sends a control signal to control the temperature control subsystem by causing at least one of the heater and the cooler to operate. In other embodiments, the communication is unidirectional, in which the temperature control system sends signals representing parameters such temperature and relative humidity to a controller. In some embodiments, signals can be communicated in both directions.

Humidity Control Subsystem

In some embodiments there is provided a humidity control subsystem that allows the control of the relative humidity in the process gas used in the system. The humidity control subsystem can be used to add water vapor to the process gas that is supplied to the curing chamber if the relative humidity is too low or if one wishes to add water to a CCM during the curing process, and it can be used to remove water vapor from process gas that exits or is exhausted from the curing chamber if the relative humidity is too high or if one wishes to extract water from a CCM during the curing process. For example, the apparatus to add water vapor can be a source of water, a valve, and a spray head or spray nozzle. In another embodiment, the apparatus to add water vapor can be a steam generator. The steam generator can include a submersible heater. In other embodiments, water vapor can be added by bubbling a gas through a water bubbler. The apparatus to remove water can be a chiller, a condenser or a heat exchanger. The humidity control subsystem includes humidity sensors that can measure the reactive humidity of the process gas at various locations in the gas flow systems, such as at the location where process gas enters or exits the curing chamber, and as appropriate, at other locations in the curing chamber or in the gas flow subsystem.

Subsystem for Controlling the Curing Process Parameters

In some embodiments, a subsystem for controlling the curing process parameters (e.g., a controller) is provided to control operational parameters for curing a CCM including controlling process step sequences, durations and timing, and for logging data measured during curing operations. In various embodiments, the controller is in communication with at least one of the source of carbon dioxide, the gas flow subsystem, the temperature control subsystem, and the humidity control subsystem. In some embodiments, the controller is in communication with sensors that provide data about the process, such as temperature, humidity, flow rates, gas pressures, gas compositions and the like. The controller is configured to control independently at least a respective one of the flow rate of the gaseous carbon dioxide, the circulation of the gas through the curing chamber, the temperature of the gas, and the humidity in the gas during a time period when the material that consumes $CO_2$ as a reactant is being cured.

In general, each subsystem can be provided as a reusable module that can be operationally connected to the other subsystems, for example using conventional off-the-shelf mechanical and electrical connectors. In some embodiments, a complete control and operations system can then be provided by assembling one or more modules of each type of subsystem as may be required for a given curing operation. For curing procedures that are expected to be carried out repeatedly, a complete control and operations system can be provided as a unit. In the event that some portion of the control and operations system malfunctions, a relatively expeditious repair can be made by substituting an entire subsystem for the malfunctioning component, and repair of that component can be conducted "off-line," e.g., without significantly affecting the curing process for a given curing operation, so that the curing process can be accomplished with only a minor deviation from the expected process duration. In particular, CCMs lend themselves to such correction of temporary malfunctions, because the CCM simply stops curing when the concentration of $CO_2$ is reduced sufficiently (e.g., when $CO_2$ is lacking in the curing gas). This is different from the curing of conventional concrete, which is initiated by the presence of water ($H_2O$), and which in general cannot be interrupted once the conventional concrete mixture becomes wet.

Turning now to FIG. 1, there is shown a schematic diagram of an embodiment of a curing system for use with $CO_2$ Composite Material. In FIG. 1 there is a gas conditioning system 102 and a curing chamber 120 which are connected together by a gas delivery tube 140 and a gas recovery tube 142. The gas conditioning system 102 includes elements of each of a source of carbon dioxide, a gas flow subsystem, a temperature control subsystem, a humidity control subsystem and a subsystem for controlling the curing process parameters. In the embodiment of FIG. 1, the gas delivery tube 140 and the gas recovery tube 142 can be any convenient size tabulation, for example a 6 inch diameter metal pipe. A gas source such as a $CO_2$ supply 130, and, as needed, sources of other gases such as air and/or water vapor are provided. The gas delivery and conditioning system can include a controller 116, such as a programmable logic controller (PLC) or another microprocessor-based controller, such as a general purpose programmable computer that can operate using a set of instructions recorded on a machine-readable medium. As illustrated in FIG. 1 a typical curing chamber 120 can include a plenum 122 that is configured to provide a gas atmosphere by way of one or more locations at which gas can be injected into the curing chamber to create a gas flow 124 having desired properties such as flow velocity or flow patterns in various portions of the curing chamber 120. The curing chamber in some embodiments will be as simple as an enclosure that can contain a CCM to be processed and process gas with an inlet and an outlet to allow the gas to be introduced and as needed removed. Additional details of such systems will be provided hereinafter.

FIG. 2 is a schematic diagram of an embodiment of an alternate curing system for use with $CO_2$ Composite Material. Many of the components illustrated in FIG. 2 can be the same as those shown in FIG. 1, but there can be additional, or different, components. For example, both the embodiments of FIG. 1 and FIG. 2 use a number of thermocouples or other temperature sensors (104, 104', 104", 104''', 104'''', collectively temperature sensors 104) and a plurality of relative humidity sensors (106, 106', collectively relative humidity sensors 106), which can be for example dry-bulb wet-bulb sensors that utilize the psychrometric ratios for carbon dioxide and water vapor or dipole polarization water vapor measurement instruments or chilled mirror hygrometers or capacitive humidity sensors.

As illustrated in FIG. 2, the $CO_2$ supply 130 can be connected to the $CO_2$ inlet by way of different flow control pathways, such as valves 210, 212, and 214 which may be used to provide a high flow rate, for example during a purging cycle, or by way of valves 220, 222, flow controller 224, and valve 226 which may be used to provide a more precisely controlled flow rate (typically having a slower flow rate than that used in a purge cycle). In the embodiment shown in FIG. 2, the piping used to connect the gas conditioning system 102 can be larger than that used in the system illustrated in FIG. 1. For example, the piping can be 8 inch pipe. Another difference is the size of heaters used to heat the gas provided to the curing chamber, which in FIG. 1 is illustrated as six 1,3 kW heaters (114), while the heating system in FIG. 2 includes eighteen 1.8 kW heaters (214). As will be understood, in any particular system the precise capacities of the various components will be sized in relation to the intended amount of material to be cured in the curing chamber 120.

The controller 116 can receive data from the temperature sensors 104 and the relative humidity sensors 106, and can communicate bi-directionally (e.g., take data from and send commands to) the valves, the chiller (or cooler) 110, the chiller (or cooler) heat exchanger 112, the blower 108, the heaters (114, 214) and the $CO_2$ supply 130 so as to be able to log data as a function of time, make determinations regarding the state of curing of a load in the curing chamber 120, and take corrective or predetermined actions so as to control the curing process. The controller 116 can also receive commands from a user, display information to the user, and record data and the commands that may be issued from time to time so that a record of the curing process may be produced in machine-readable form for later use.

Gas Flow in the Curing Chamber

The gas flow in the curing chamber in various embodiments can include gas flows external to the body, gas flows internal to the body, gas flows through a porous or pervious body, or combinations of such gas flows. The gas delivery system includes the gas delivery tube 140, the gas recovery tube 142, and the plenum 122, which can have many forms. In some embodiments, the plenum 122 directs gases to the outside of green bodies of $CO_2$ Composite Material. In other embodiments, the plenum 122 directs gases to internal passages or openings in green bodies of $CO_2$ Composite Material. In still other embodiments, the plenum 122 directs gases both to the outside of and to internal passages or openings in green bodies of $CO_2$ Composite Material.

Internal Gas Delivery System

This type of gas delivery system is comprised of linked, gridded piping having a specific spacing and size, which delivers gas, or fluid through a series of holes distributed throughout the piping system, to a surrounding $CO_2$ Composite Material body. The supply of gas (including carbon dioxide) is then regulated to match or come close to matching the sequestration rate of $CO_2$ in the $CO_2$ Composite Material. This is one method to rapidly cure a section of $CO_2$ Composite Material. In the typical internal gas delivery system, the piping system is left imbedded in the $CO_2$ Composite Material sample after it is cured. The piping system can act additionally as a means of reinforcement, and can provide the ability to perform cleaning or maintenance of $CO_2$ Composite Material via a compressed air or water backwashing technique.

Some of the benefits of this approach include but are not limited to a reduction in cure time, reduction of carbon footprint associated with a cast-in-place $CO_2$ Composite Material application, improved life of pervious $CO_2$ Composite Material sections due to the ability to backwash debris out of pervious $CO_2$ Composite Material and the presence of a reinforcing grid. Standard practice for the placing of pervious concrete with Portland cement based systems calls for a 7-28 day curing period before the area can be used. With the gas delivery system, final strength of a $CO_2$ Composite Material can be achieved in as little as 1 day. In the trial outlined below a supply of $CO_2$ is regulated at 1.7 kg per hour. The result after 22 hours was a carbonation extent of 40% in relation to the potential of the $CO_2$ Composite Material to carbonate. This correlates to 43% $CO_2$ efficiency. Based on this data, we can control the gas supply rate to match the sequestration rate of the $CO_2$ Composite Material thereby improving the efficiency of $CO_2$ usage and optimizing the time needed to effect the curing process.

An embodiment of an internal gas delivery system for curing elongate specimens such as railroad ties is now described.

Figure 3:
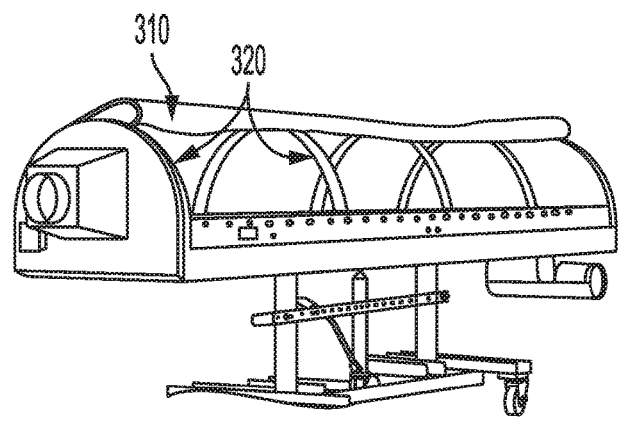
FIG. 3 is a perspective view of a curing chamber suitable for curing elongate specimens of $CO_2$ Composite Material.

FIG. 3 is a perspective view of a curing chamber suitable for curing elongate specimens of $CO_2$ Composite Material. The curing chamber in FIG. 3 has a flexible wall 310 that is supported by frame members 320. The closure of flexible wall 310 may be accomplished by the use of weights, or by the use of magnetic stripping and magnetic frame members. Other flexible wall systems are described in more detail hereinafter.

Figure 4:
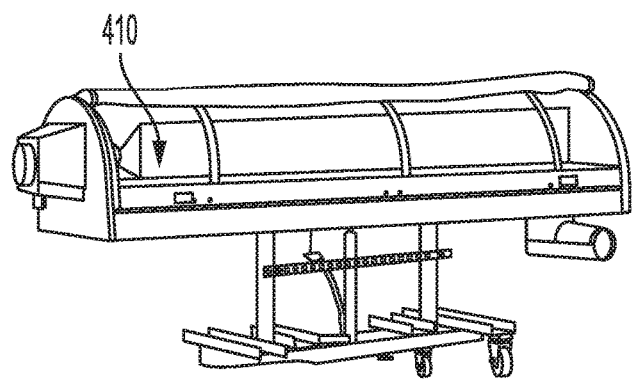
FIG. 4 is a view of the curing chamber of FIG. 3 containing an elongate specimen of $CO_2$ Composite Material to be cured.

FIG. 4 is a view of the curing chamber of FIG. 3 containing an elongate specimen 410 (a railroad tie) of $CO_2$ Composite Material to be cured.

Figure 5:
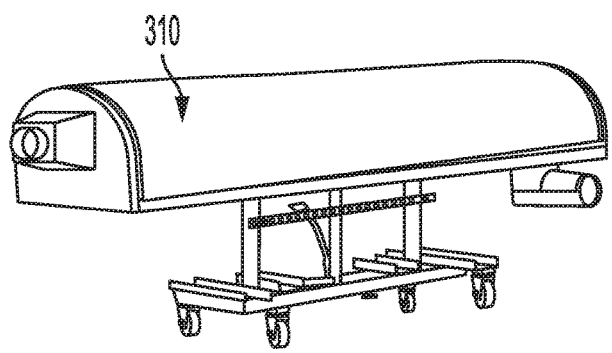
FIG. 5 is a view of the curing chamber of FIG. 3 when closed to allow curing to be performed.

FIG. 5 is a view of the curing chamber of FIG. 3 when closed to allow curing to be performed. The flexible wall 310 is fully deployed in this view.

In using a system as shown in FIG. 3 through FIG. 5, the process gas is supplied to at least one internal aperture that traverses the length of the CCM to be cured. The curing can then proceed from the inside of the green body toward the outside. Data has been obtained for such curing processes.

Figure 6:
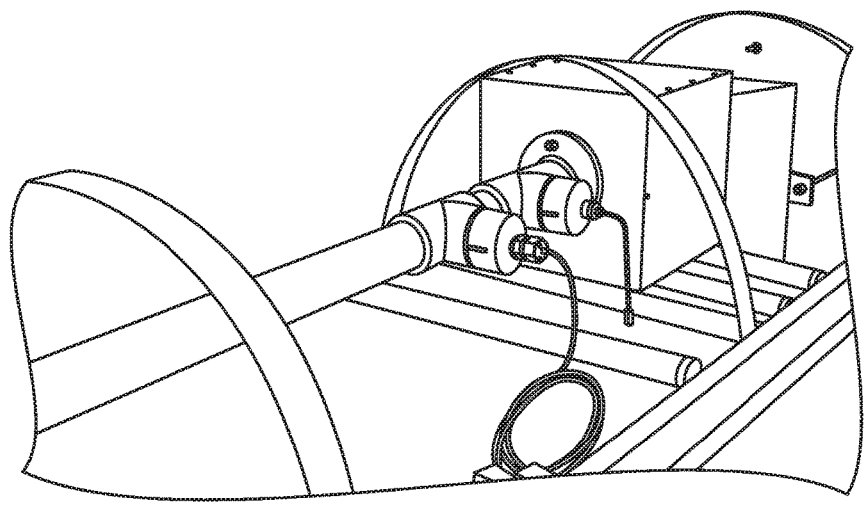
FIG. 6 is an image of a plenum used to deliver a curing atmosphere to a sample of $CO_2$ Composite Material having an interior circular channel.

FIG. 6 is an image of a plenum used to deliver a curing atmosphere to a sample of $CO_2$ Composite Material having an interior circular channel. As may be seen in FIG. 6, the plenum 610 is a pipe having a circular cross section that can be placed in fluid communication with a circular channel in a sample of $CO_2$ Composite Material to be cured.

Figure 7:
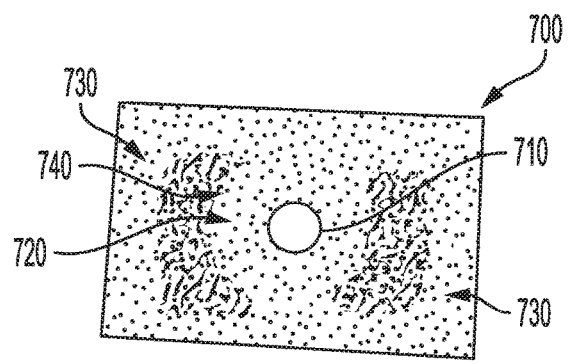
FIG. 7 is an image of a sample of $CO_2$ Composite Material that was cured using flow in an interior circular channel.

FIG. 7 is an image of a sample 700 of $CO_2$ Composite Material that was cured using flow in an interior circular channel 710 and gas flow on the exterior of the sample. As shown in FIG. 7, the sample 700 has a circular region 720 that has been cured, a rectangular peripheral region 730 that has been cured, and an uncured region 740 between the cured regions 720 and 730. This demonstrates the ability to cure the CCM from the inside using internal process gas flow and from the outside using gas flow exterior to the sample.

Figure 8:
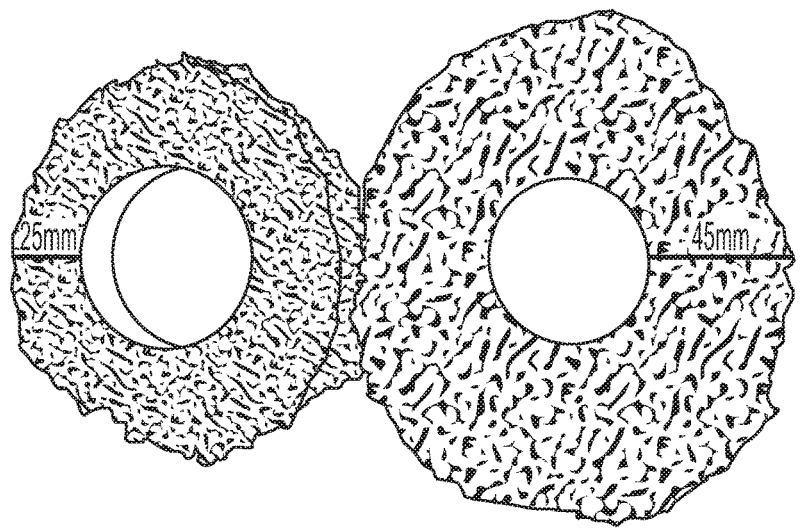
FIG. 8 is an image that illustrates the difference in reaction depth as a function of flow rate.

FIG. 8 is an image that illustrates the difference in reaction depth as a function of flow rate. In FIG. 8 it is apparent that for the geometry examined, a higher flow rate led to a greater depth of cure in the same time interval.

Figure 9:
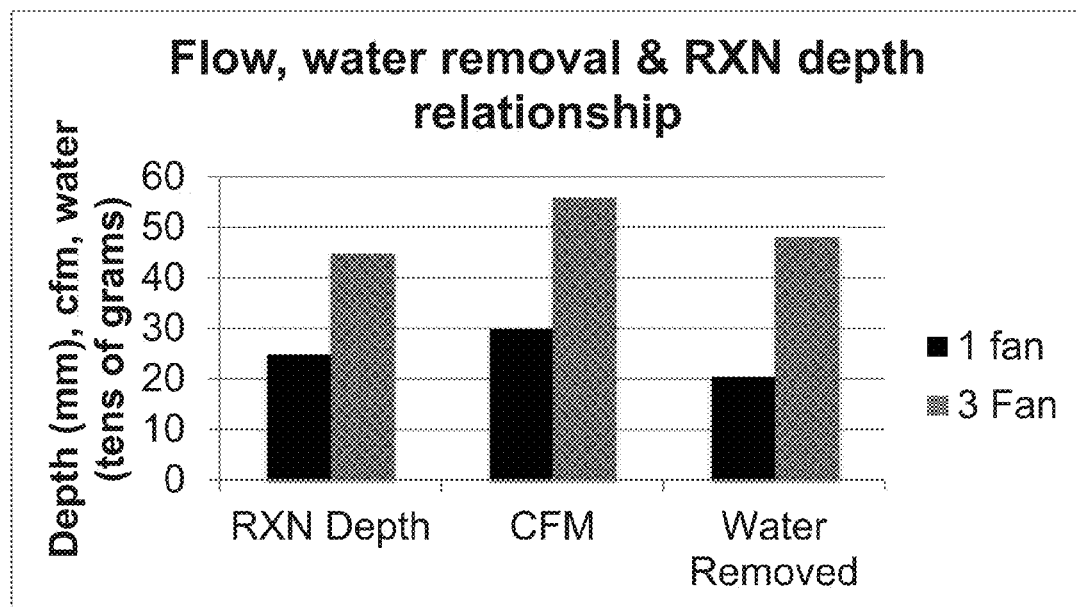
FIG. 9 is a graph that illustrates the differences in reaction depth, gas flow in cubic feet per minute and amount of water removed from specimens of $CO_2$ Composite Material cured in systems using 1 fan and 3 fans.

FIG. 9 is a graph that illustrates the differences in reaction depth, gas flow in cubic feet per minute and amount of water removed from specimens of $CO_2$ Composite Material cured in systems using 1 fan and 3 fans. It is apparent that reaction depth, gas flow in cubic feet per minute and amount of water removed from specimens of $CO_2$ Composite Material all increase when more capacity to move the reactive gas is provided.

Figure 10:
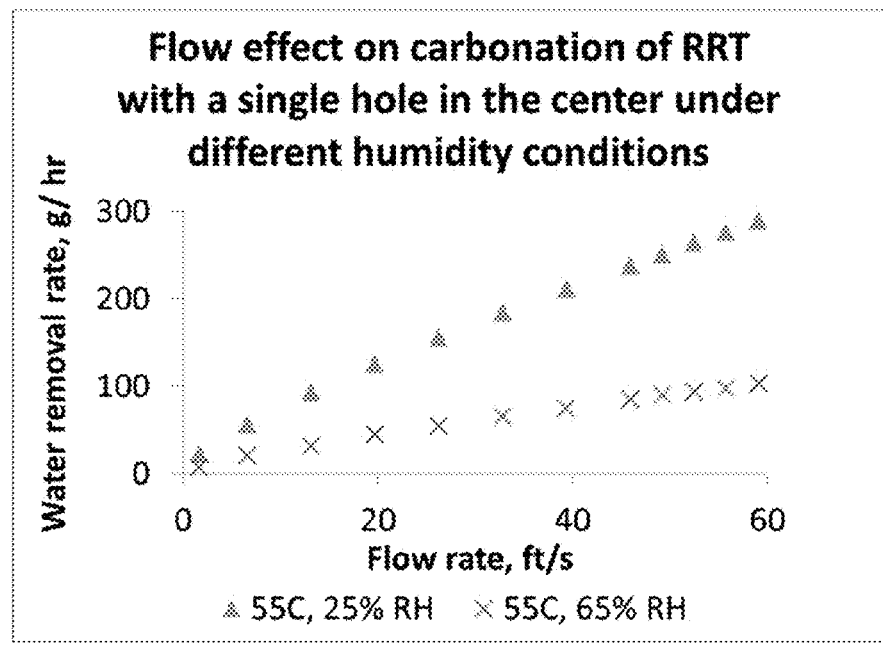
FIG. 10 is a graph showing data for water removal rate as a function of flow rate for gases having different relative humidity.

FIG. 10 is a graph showing data for water removal rate as a function of flow rate for gases having different relative humidity. As is seen in FIG. 10, using a higher flow rate and a lower relative humidity tends to increase the rate at which water is removed from the sample. It is believed that the reaction of CCM with $CO_2$ occurs preferentially at the interface where water-saturated CCM is in contact with gaseous $CO_2$, so more rapid removal of water correlates with faster rates of cure.

Example—Cure Pervious $CO_2$ Composite Material in Place

The process of curing pervious $CO_2$ Composite Material in place is shown in FIG. 11 through FIG. 16. This is an installation that was made on the ground to one side of a building. It is an example of a true outdoor cast in place application in use.

Figure 11:
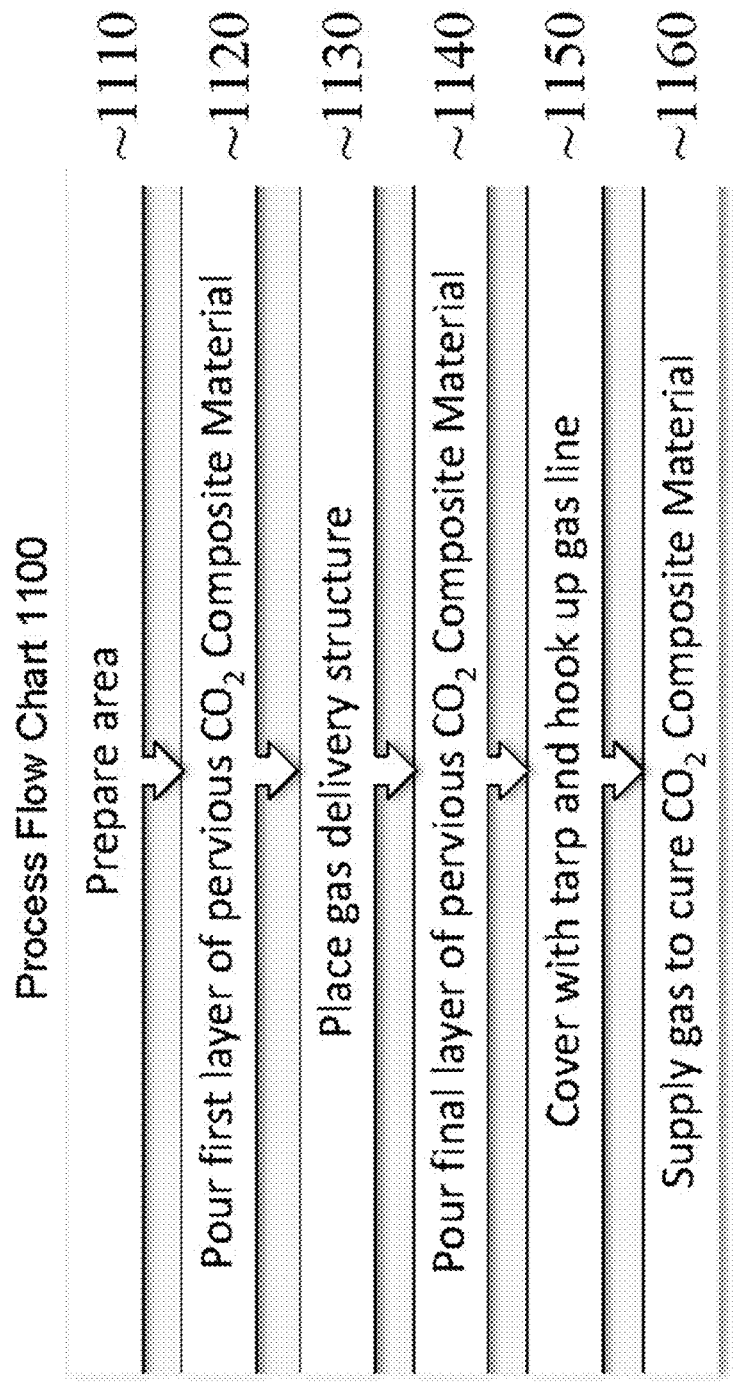
FIG. 11 is a process flow chart illustrating the steps in a process of placing and curing a composite material in an outdoor location.

FIG. 11 is a process flow chart illustrating the steps in a process of placing and curing a composite material in an outdoor location. The process can be divided into steps. In step 1110, one prepares the area where the $CO_2$ Composite Material is to be installed and cured. This can include digging, grading, setting out forms, and the like. In step 1120, one pours or otherwise installs a first layer of pervious $CO_2$ Composite Material. The activity of installing the $CO_2$ Composite Material includes forming the body to be cured using any one or more of casting, pouring, vibrating, pressing, and the like, depending on the $CO_2$ Composite Material formulation or mix workability.

Figure 12:
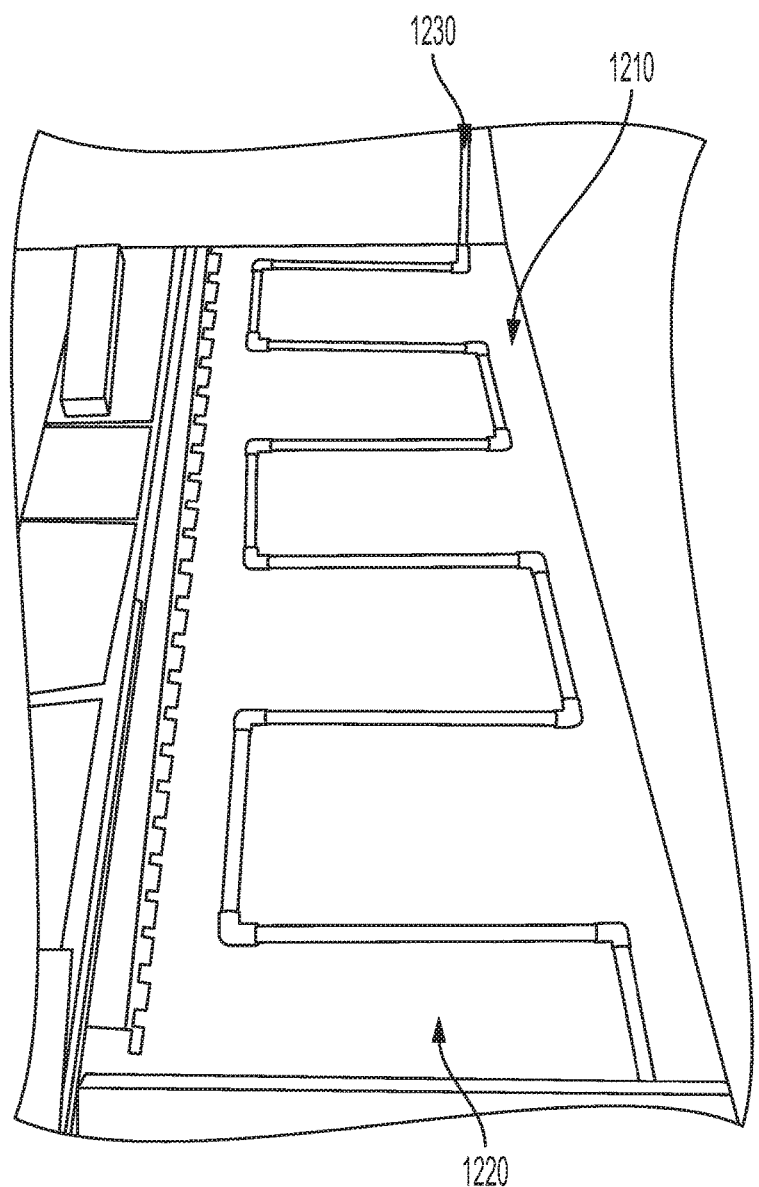
FIG. 12 is an image that illustrates a perforated PVC grid used for gas delivery to a cast-in-place section of pervious $CO_2$ Composite Material.

In step 1130, one places or installs a gas delivery structure, which in some embodiments can be a tube or pipe with holes defined in a wall thereof. FIG. 12 is an image that illustrates a perforated PVC grid 1210 used for gas delivery to a cast-in-place section of pervious $CO_2$ Composite Material. The first layer 1220 of material to be cured is also seen, as can a gas connection point 1230.

Figure 13:
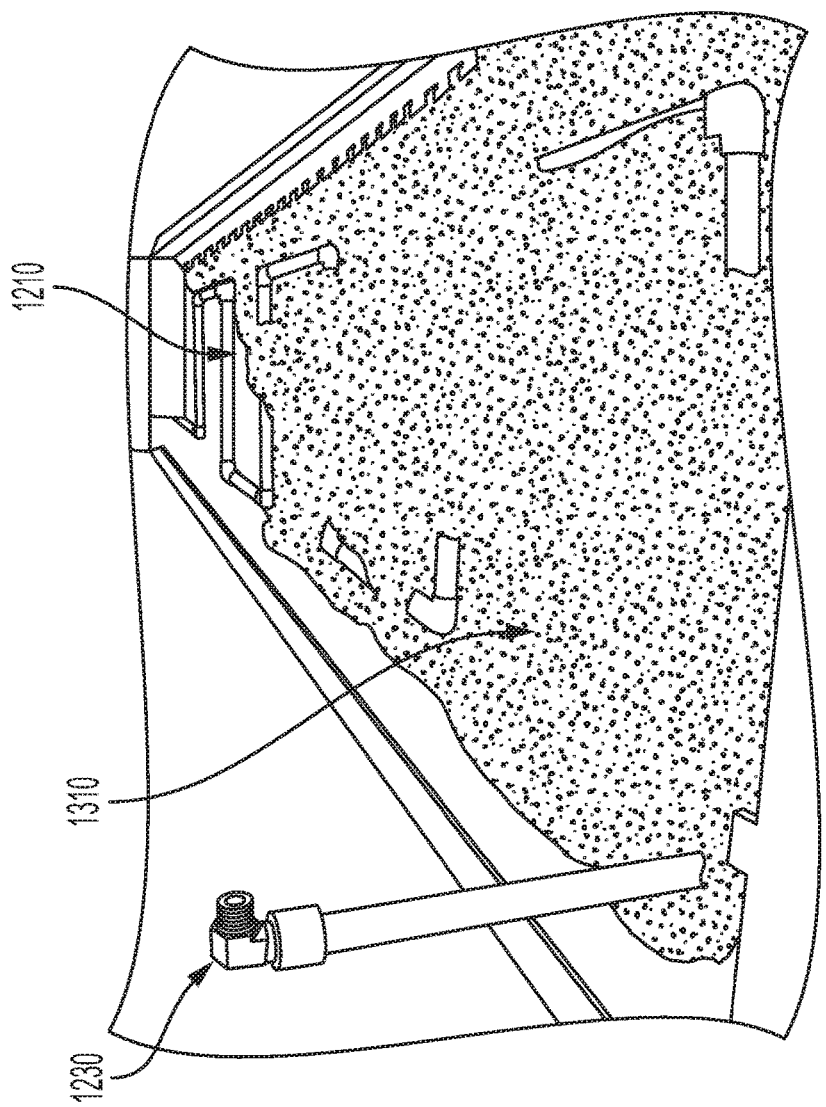
FIG. 13 is an image that illustrates pervious $CO_2$ Composite Material being poured over the gas delivery system of FIG. 12.

In step 1140, one pours or installs a second (final) layer of pervious $CO_2$ Composite Material over the gas delivery structure. FIG. 13 is an image that illustrates pervious $CO_2$ Composite Material 1310 being poured over the gas delivery system 1210 of FIG. 12. However, it should be understood that the installation of the gas delivery structure and the material to be cured at the desired location can be performed in any order, including placing the gas delivery structure in place first, and then placing the material to be cured thereafter, or first placing the material to be cured and then installing the gas delivery structure.

Figure 14:
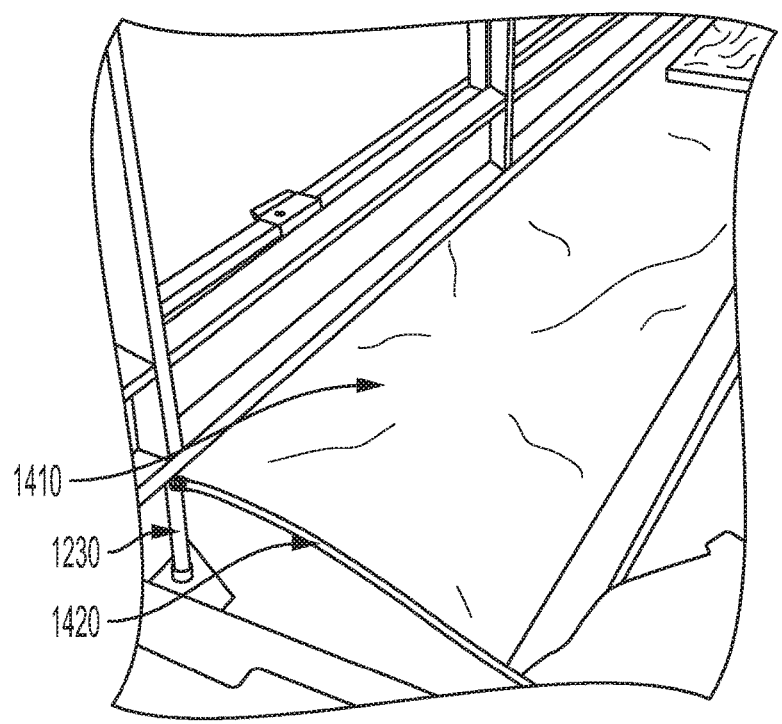
FIG. 14 is an image that illustrates a section of pervious $CO_2$ Composite Material that is covered with plastic sheeting and that has a $CO_2$ inlet connected thereto.

In step 1150, one covers the installed material, for example with a tarpaulin (a "tarp") and one hooks up the gas line. FIG. 14 is an image that illustrates a section of pervious $CO_2$ Composite Material that is covered with plastic sheeting 1410 and that has a $CO_2$ inlet 1420 connected to gas connection point 1230.

Before the installed mixture is cured it may be necessary to dry or remove excess water from the uncured $CO_2$ Composite Material using one or more of air drying, draining, or gas recirculation conditioning to get the material to the proper conditions to begin the curing process. In some embodiments, it may be necessary to add water to a dry mixture of uncured $CO_2$ Composite Material.

Figure 15:
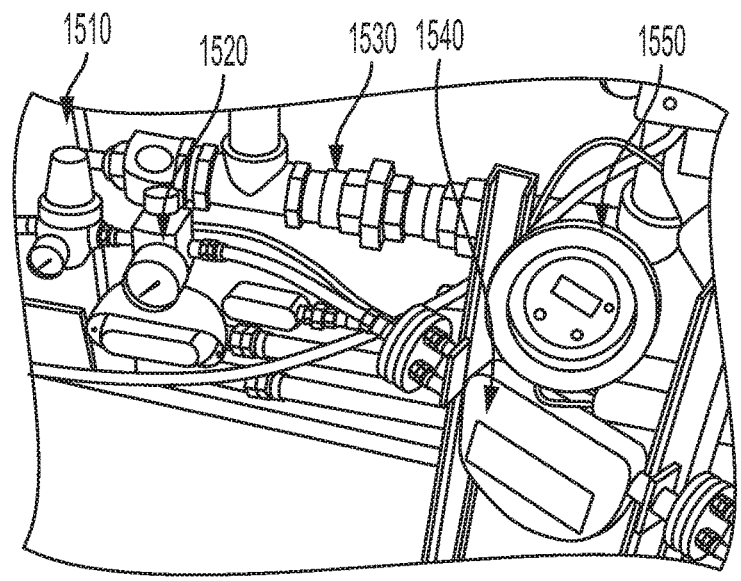
FIG. 15 is an image that shows gas flow regulators and a flow meter used to control the $CO_2$ supply to the pervious $CO_2$ Composite Material section of FIG. 14.

In step 1160, one supplies gas to cure the $CO_2$ Composite Material. FIG. 15 is an image that shows gas flow regulators and a flow meter used to control the $CO_2$ supply to the pervious $CO_2$ Composite Material section of FIG. 14. In FIG. 15, there are seen a high pressure regulator 1510, low pressure regulator 1520, gas delivery piping 1530, a $CO_2$ mass flow meter 1540, and a $CO_2$ mass flow meter readout 1550.

Figure 16:
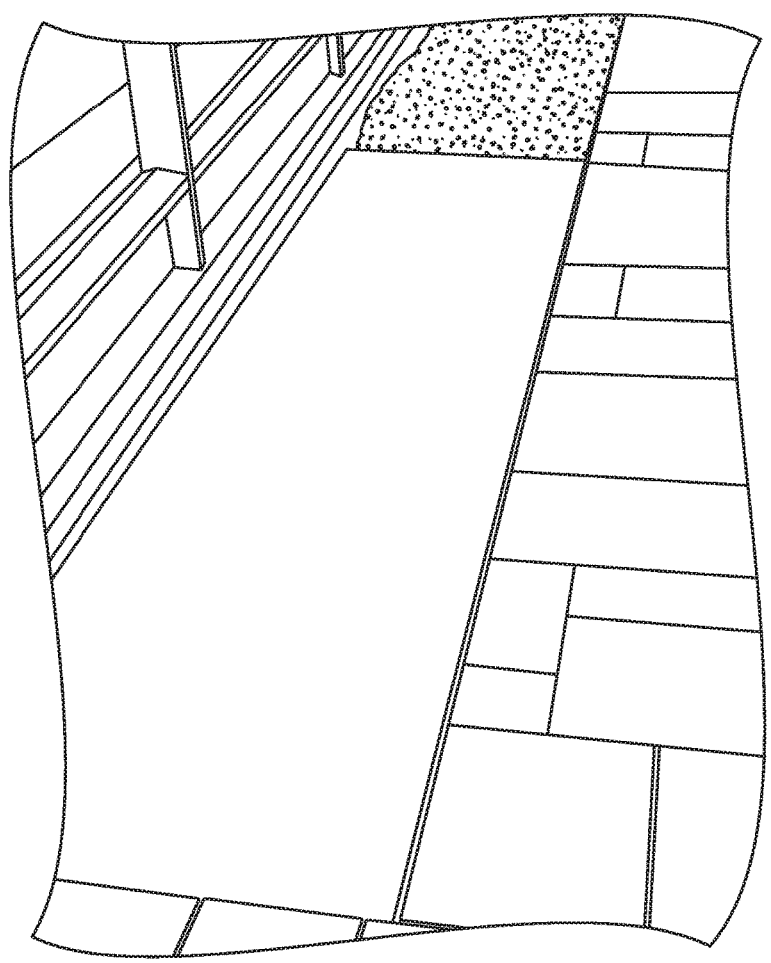
FIG. 16 is an image that shows a cured section of pervious $CO_2$ Composite Material after 22 hours using the embedded $CO_2$ delivery system of FIG. 12.

FIG. 16 is an image that shows a cured section of pervious $CO_2$ Composite Material after 22 hours using the embedded $CO_2$ delivery system of FIG. 12.

In some embodiments, sensors can be positioned within the volume of the $CO_2$ Composite Material to be cured so that operational parameters during the curing process may be monitored. Such sensors are in general sacrificial or "one time use sensors" in that they are generally not removed and recovered after the $CO_2$ Composite Material has been cured, but rather are permanently fixed in the $CO_2$ Composite Material.

Example:Cast-in-Place Curing System

A cast-in-place curing system involves systems and methods for carbonating a $CO_2$ Composite Material in the absence of any sealed vessel. This "cast-in-place" curing technique involves the use of a gas permeable barrier being used as a layer to allow $CO_2$ to diffuse through a cast section of $CO_2$ Composite Material. This is a procedure for rapid strength generation and the permanent sequestration of carbon dioxide gas, leading to a reduction in the carbon footprint associated with cast-in-place concrete applications. This process is less energy intensive than all previous carbonation curing techniques as no temperature-controlled or sealed vessel is needed. It has been demonstrated for the first time that a significant level of strength (+2,000 psi) can be achieved using the described cast-in-place techniques with a dense $CO_2$ Composite Material.

$CO_2$ Composite Material has been carbonated via "bottom-up" carbonation curing process. This trial involved successful carbonation without the use of a sealed vessel to produce a $CO_2$ Composite Material slab having compressive strengths in excess of 2,000 psi.

We have used of Enkavent® material to create a gas permeable layer for providing a larger $CO_2$ delivery surface to allow for carbonation in a cast-in-place system.

Figure 17:
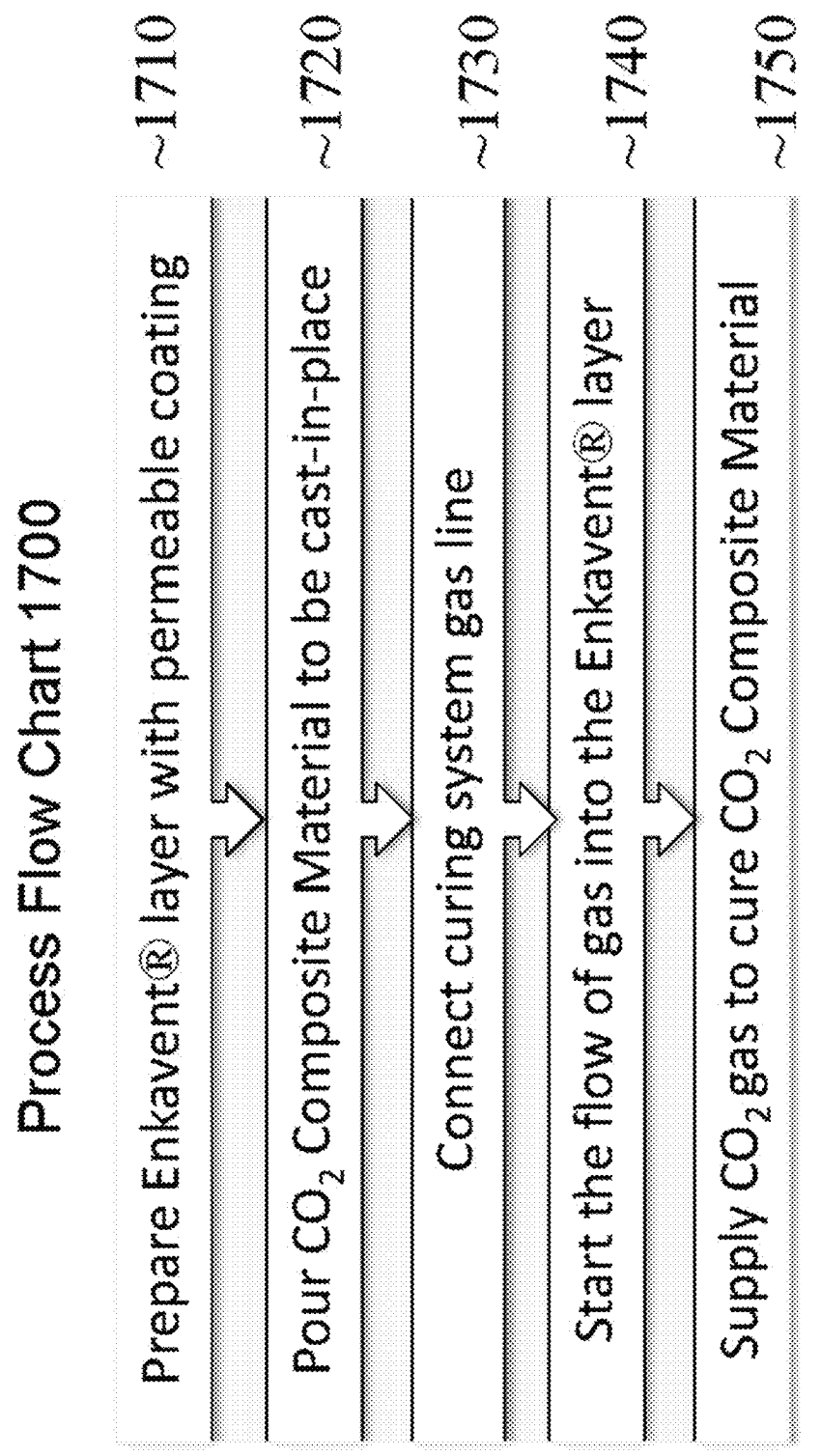
FIG. 17 is a process flow chart illustrating the steps of placing and curing $CO_2$ Composite Material using the cast-in-place process.

FIG. 17 is a process flow chart illustrating the steps of placing and curing $CO_2$ Composite Material using the cast-in-place process. In step 1710 one prepares an Enkavent® layer with permeable coating by positioning the material in the location where the $CO_2$ Composite Material is to be cast and cured. In step 1720 one pours (or otherwise places) the $CO_2$ Composite Material to be cast-in-place. In step 1730 one connects a curing system gas line in fluid communication with the Enkavent® layer. In step 1740 one starts the flow of gas into the Enkavent® layer. In step 1750 one supplies $CO_2$ gas to cure $CO_2$ Composite Material for a time period long enough to effect the cure desired.

Figure 18:
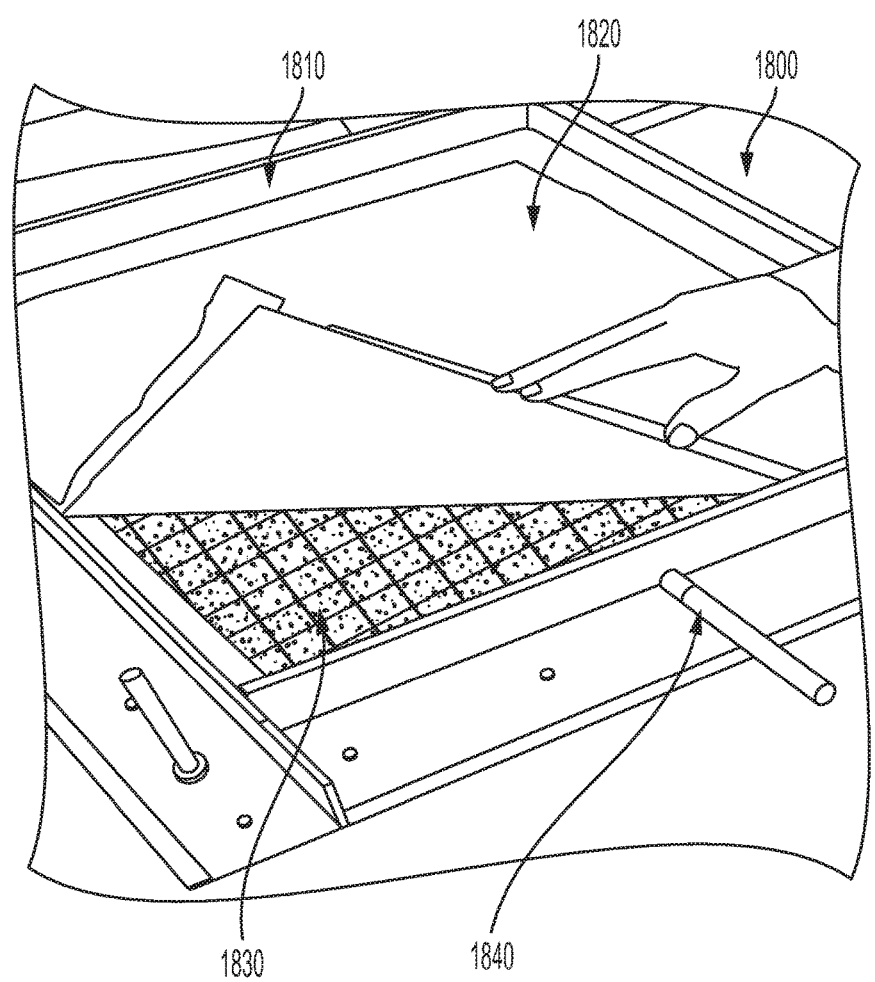
FIG. 18 is an image showing a mold that allows $CO_2$ delivery to and through Enkavent® material.

FIG. 18 is an image showing a mold 1800 that allows $CO_2$ delivery to and through Enkavent® material, in which the frame 1810 is arranged to contain the $CO_2$ Composite Material in a desired size and shape. As seen in FIG. 18, the mold 1800 has a gas delivery line 1840 that introduces process gas below a porous screen 1830 that supports a layer of Enkavent® material 1820. Enkavent® material is available from available commercially from Enka Geomatrix Systems, a Division of BASF Corporation of Enka, N.C., and its successor, Colbond, Inc. Enkavent® material is described in more detail in U.S. Pat. Nos. 4,212,692, 5,960, 595 and 6,487,826. The $CO_2$ Composite Material is positioned adjacent the Enkavent® material.

Figure 19:
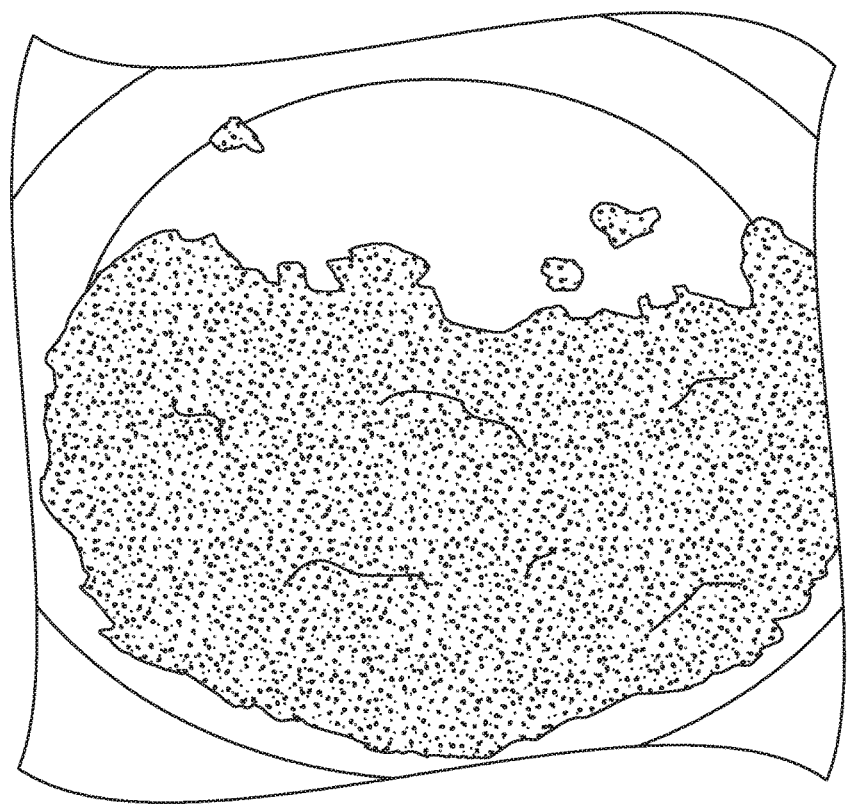
FIG. 19 is an image showing uncured $CO_2$ Composite Material mix for use in a cast-in-place process.

FIG. 19 is an image showing uncured $CO_2$ Composite Material mix for use in a cast-in-place process.

Figure 20:
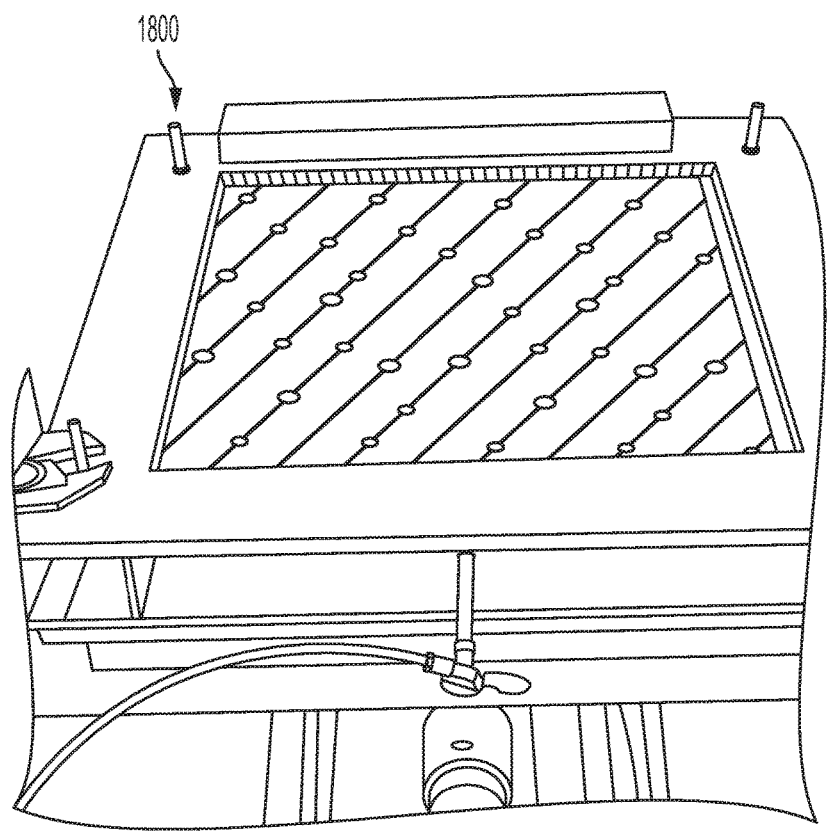
FIG. 20 is an image showing a mold 1800 after casting a $CO_2$ Composite Material and connection of the process gas line for curing the $CO_2$ Composite Material with $CO_2$.

FIG. 20 is an image showing a mold 1800 after casting a $CO_2$ Composite Material and connection of the process gas line for curing the $CO_2$ Composite Material with $CO_2$.

Figure 21:
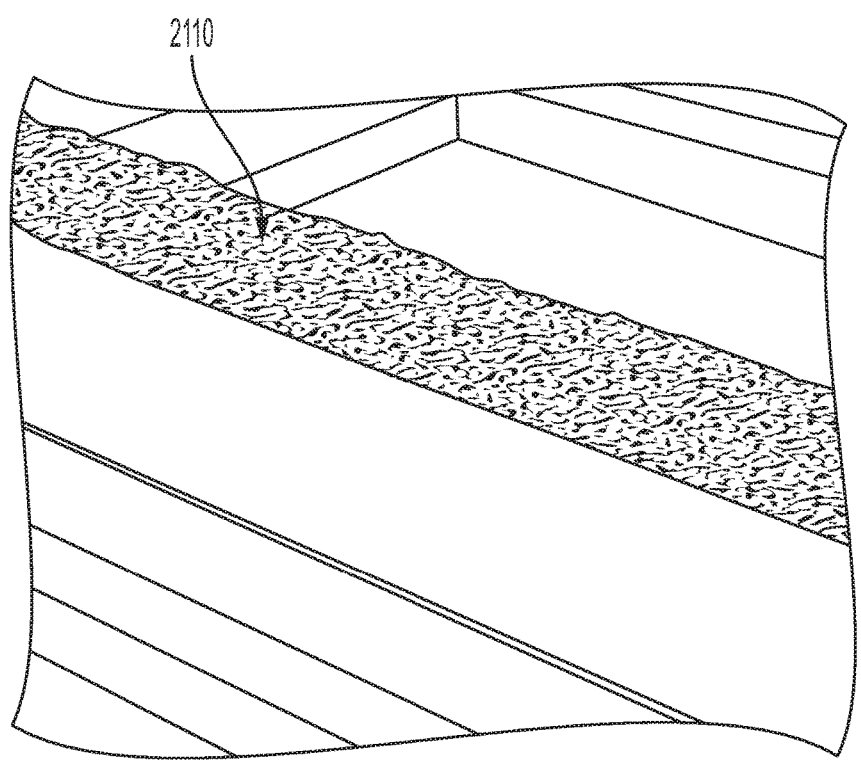
FIG. 21 is an image showing a section cut from a slab of $CO_2$ Composite Material after carbonation curing.

FIG. 21 is an image showing a section 2110 cut from a slab of $CO_2$ Composite Material after carbonation curing.

Flexible-Wall Curing Chamber

Figure 22:
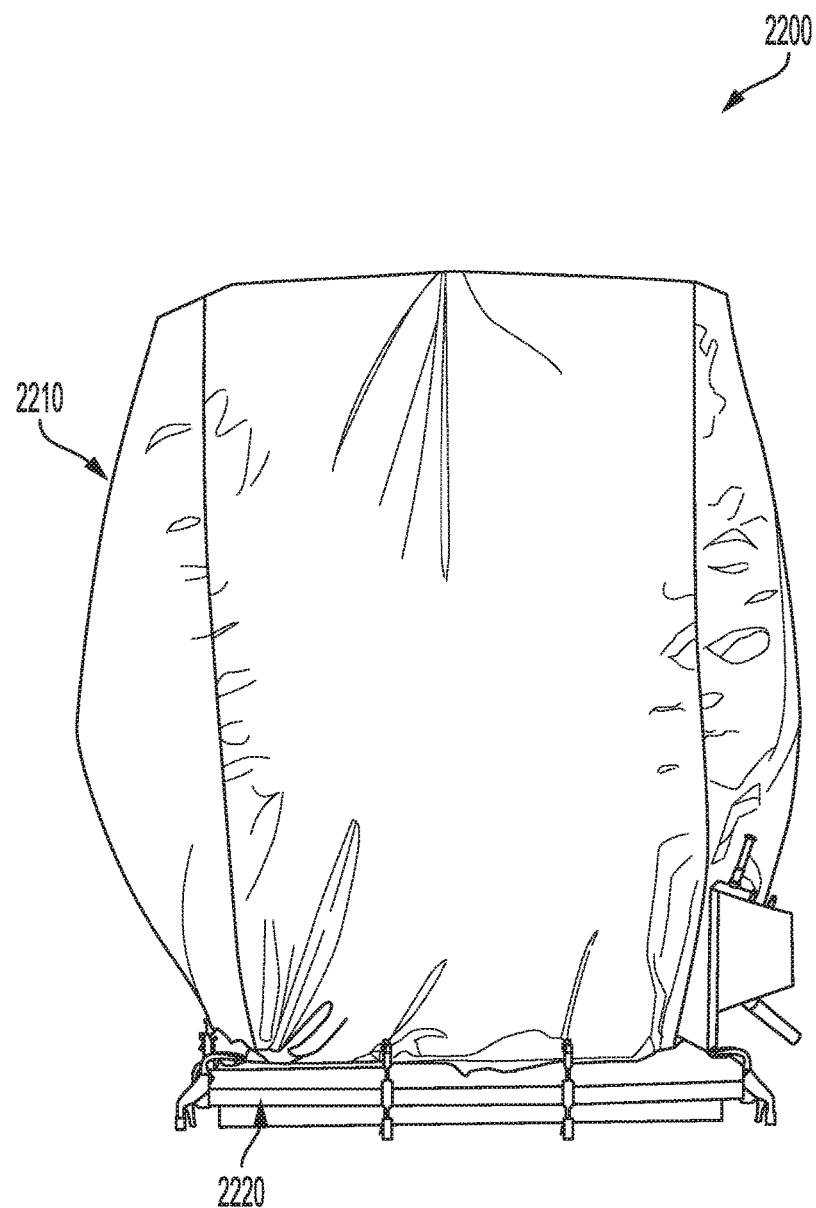
FIG. 22 is a view of a curing chamber made of flexible material.
Figure 23:
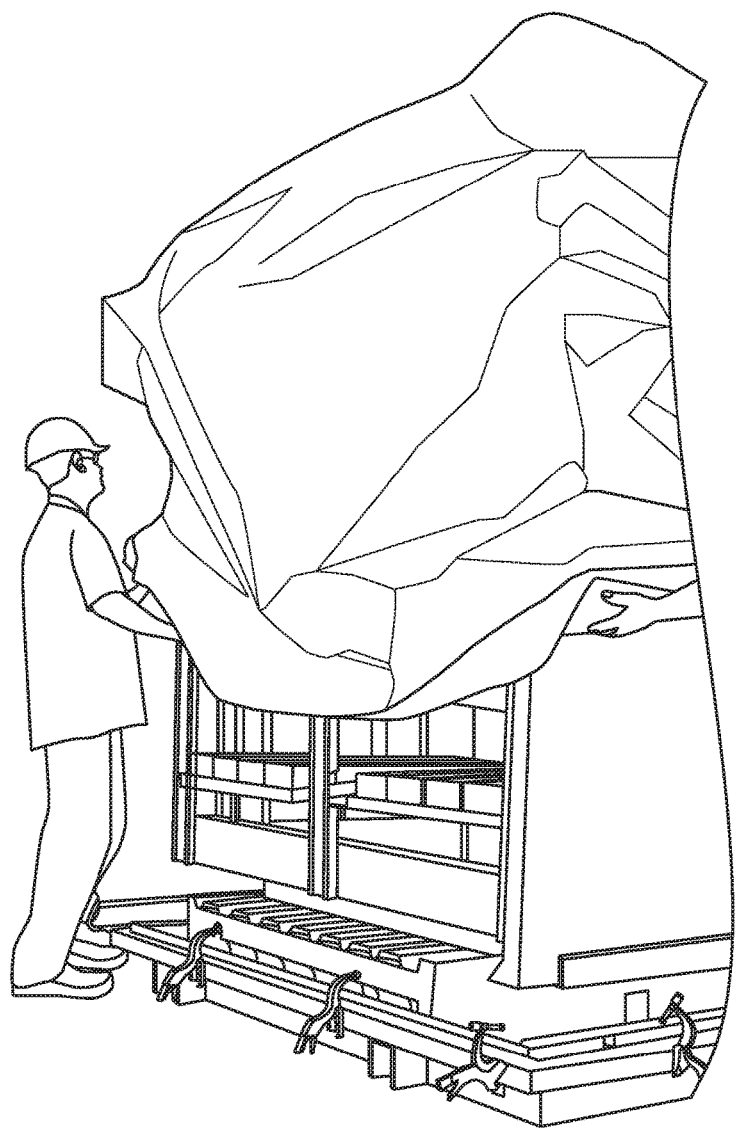
FIG. 23 is a view of the flexible material being installed to form the curing chamber of FIG. 22.
Figure 24:
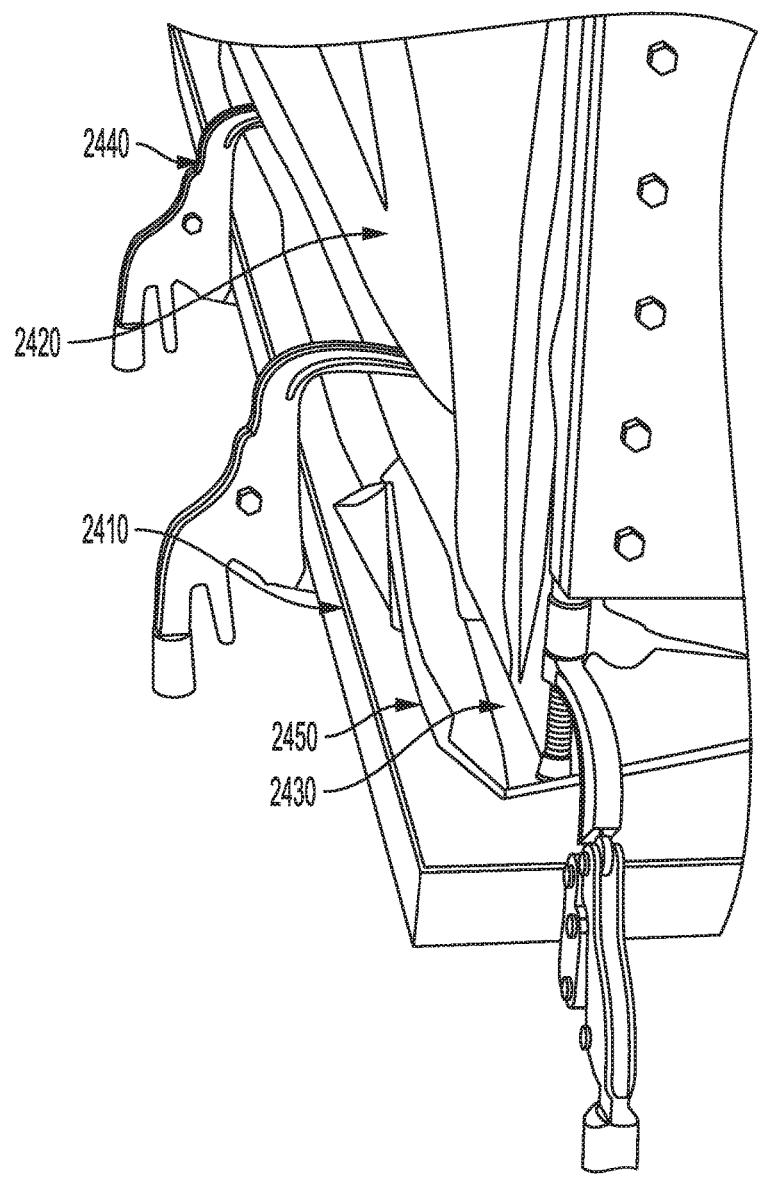
FIG. 24 is a view of a clamping method for holding the flexible material of the curing chamber of FIG. 22 to a rigid support.

Another type of curing chamber that can be employed to cure specimens of $CO_2$ Composite Material is illustrated in FIG. 22 through FIG. 24. This is a chamber made from a flexible material, such as plastic sheet material, to form a chamber having flexible walls. In a preferred embodiment the flexible material may be coated with a reflective layer, such as aluminum, so as to be reflective of infrared radiation. Similar material is commonly used in blankets or ponchos used in human rescue operations, or given to marathon runners at the end of a race so that the person's body heat can be more easily retained. In the embodiments described next, the wall is provided to contain a gas used in curing specimens of $CO_2$ Composite Material placed within the chamber so that the properties of the gas, such as composition, temperature, relative humidity and flow rate, can be controlled. In some embodiments, sensors may be situated within the chamber to provide data about the properties of the gas and the conditions within the chamber during a curing operation.

FIG. 22 is a view of a curing chamber 2200 made of flexible material 2210 that is attached to a rigid base 2220 by a clamping system. In one embodiment, the flexible material is metalized plastic sheet. Other materials that can be used as the flexible material are Mylar® and latex.

FIG. 23 is a view of the flexible material being installed to form the curing chamber of FIG. 22.

FIG. 24 is a view of a clamping method for holding the flexible material of the curing chamber of FIG. 22 to a rigid support. As illustrated in FIG. 24, a rigid base 2410 and a flexible sheet 2420 are connected by the use of rigid rods 2430 and clamps 2440. In the embodiment shown the rigid rods 2430 have square or rectangular cross sections. In some embodiments a deformable gasket 2450 may be placed between the mating surfaces of the rigid base 2410 and the flexible sheet 2420 so as to provide a more hermetic seal. The gasket 2450 can be any material that is chemically compatible with the curing gas and that is sufficiently soft so that it forms a substantially hermetic seal when compressed between the mating surfaces of the rigid base 2410 and the flexible sheet 2420. Examples of such materials that can be used as gaskets are closed cell plastic foam sheet and viscous liquids such as petroleum based gels. In other embodiments, a channel filled with a liquid that is compatible with the curing atmosphere, such as water, can be provided at the location in which the mating surfaces of the rigid base 2410 and the flexible sheet 2420 are situated.

Figure 25:
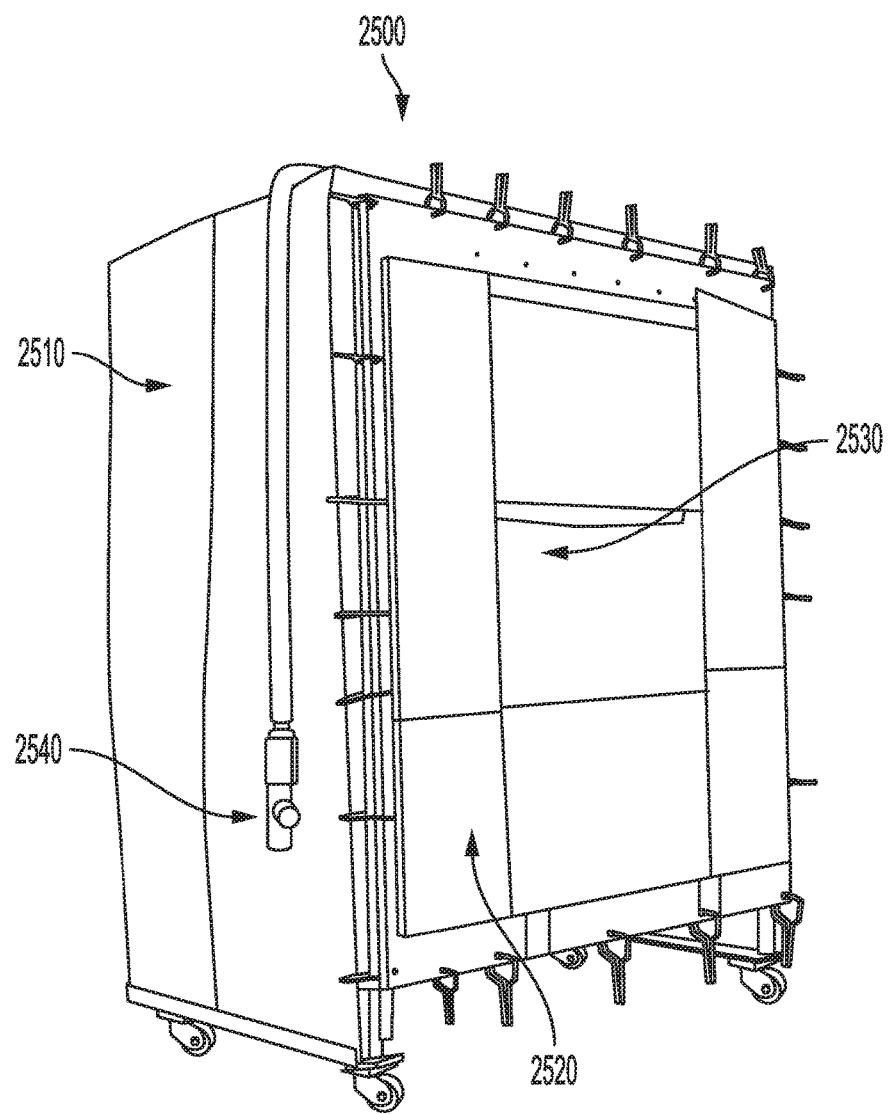
FIG. 25 is a view of another embodiment of a curing chamber having some flexible walls and some relatively rigid walls.

FIG. 25 is a view of another embodiment of a curing chamber 2500 having some flexible walls 2510 and some relatively rigid walls 2520. In the embodiment shown in FIG. 25, the aperture 2530 may be covered with a material that is transparent in a spectral region of interest, such as the visible or the infrared, so that visual observations or instrument-based electromagnetic radiation observations, such as optical pyrometry or gas flow or gas composition measurements may be made. 2540 is a fitting used to make a connection to a gas conditioning system 102 as previously described (e.g., 2540 is used as the connection to one of a gas delivery tube 140 and a gas recovery tube 142).

Modular Gas Handling System

Figure 26:
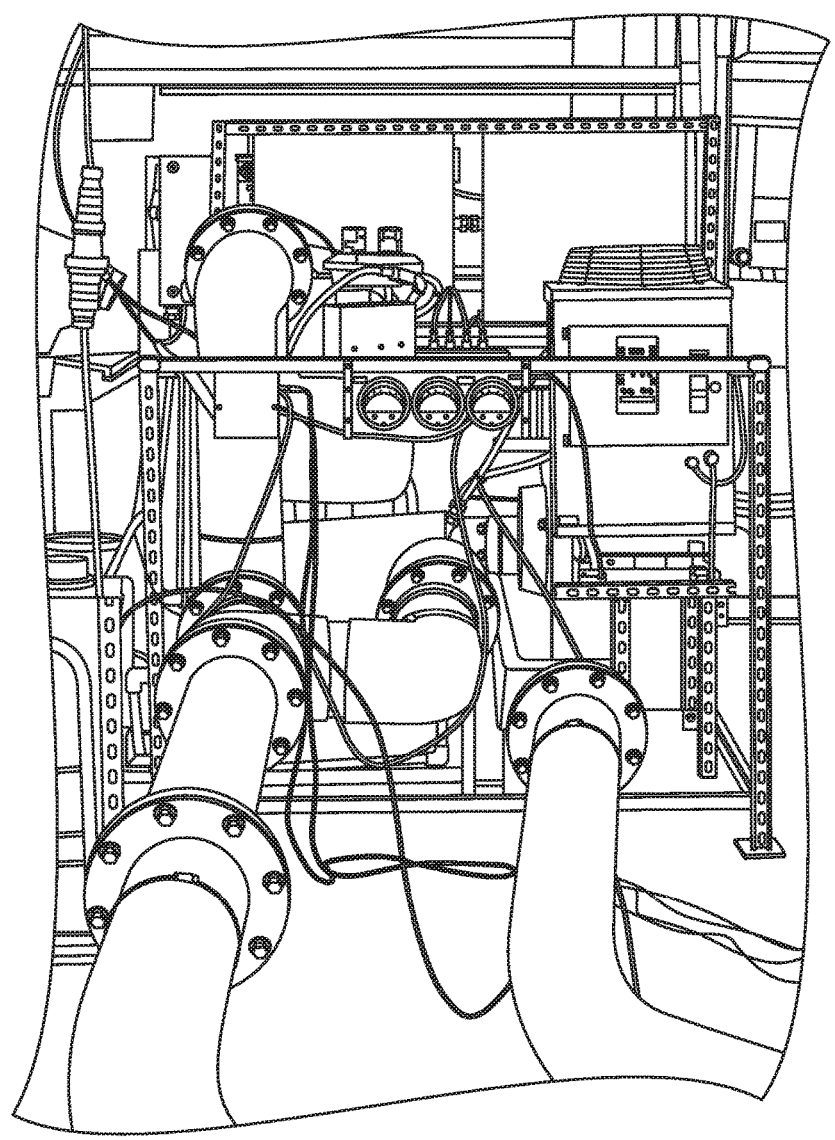
FIG. 26 is a view of a modular gas handling system that can be used with various curing chambers.

FIG. 26 is a view of a modular gas handling system that can be used with various curing chambers.

Figure 27:
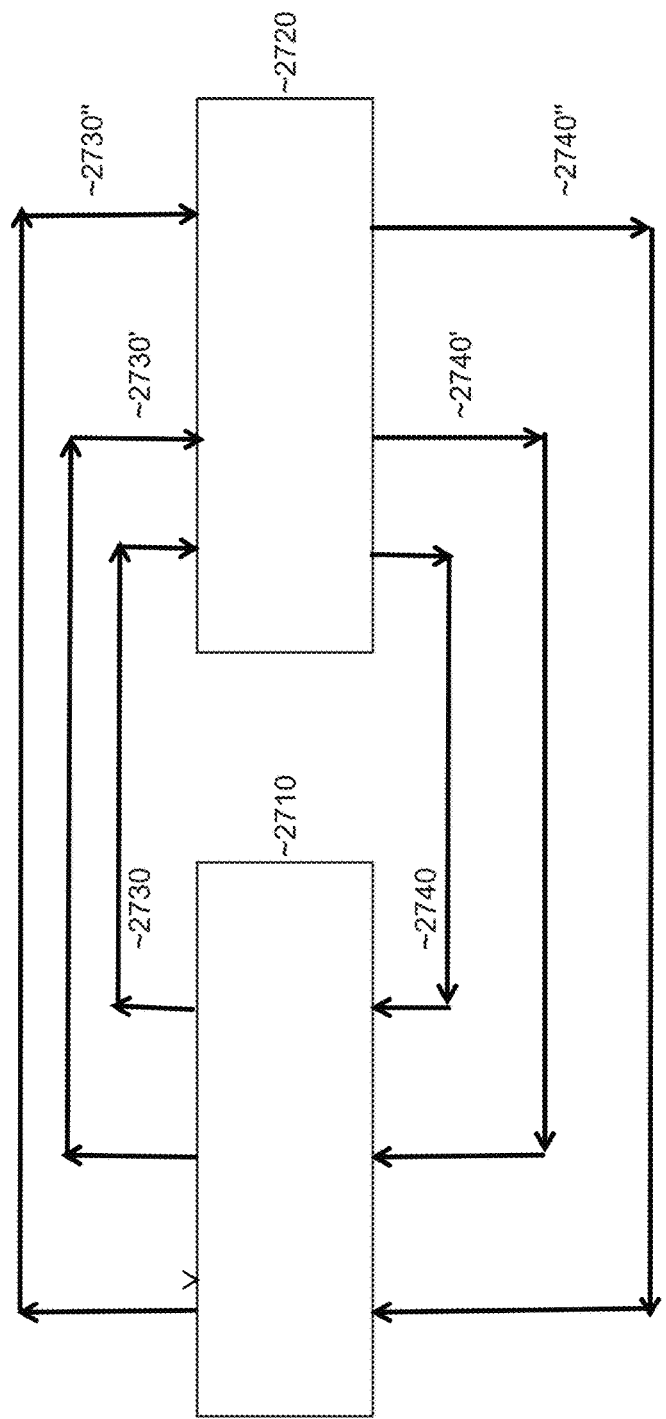
FIG. 27 is a schematic diagram showing a gas handling system that has multiple gas delivery ports and multiple gas recovery ports.

FIG. 27 is a schematic diagram showing a gas handling system 2710 that has multiple gas delivery ports 2730, 2730', 2730" and multiple gas recovery ports 2740, 2740', 2740" by way of which it in fluid communication with a curing chamber 2720. The modular gas handling system of FIG. 27 can be viewed as a multiple number of modular gas handling systems of FIG. 26 that operate in parallel under the control of a controller. The gas handling system of FIG. 27 can be used to provide gas flows having individually controlled flow rates, gas compositions and gas temperatures so that gas glows that are tailored to specific regions of a single curing chamber can be provided and controlled. As needed, multiple sets of sensors can be provided so that each gas flow stream can be individually monitored and controlled.

Computer-Based Control System

In order to control the operation of the curing system in a more convenient manner, there is provided at least one controller in communication with at least one of the source of carbon dioxide, the gas flow subsystem, the temperature control subsystem, and the humidity control subsystem. The at least one controller is configured to control independently during a time period when the material that consumes $CO_2$ as a reactant is being cured at least a respective one of the composition of the gas provided for the curing process, the flow rate of carbon dioxide, the rate or velocity of circulation of the gas through the curing chamber or through the CCM being cured, the direction of circulation of the gas through the curing chamber, the temperature of the gas, and the humidity in the gas.

In a preferred embodiment, the controller is a general purpose computer that is operated under a set of instructions recorded on a machine-readable medium, or a similar electronic device as described in more detail hereafter. In some embodiments, an operator can control some (or all) of the operations in a curing process by overriding the controller, or by providing specific instructions to the controller that are performed as the operator directs. For example, some of the steps in a curing process having to do with setting up the curing chamber, loading CCM material to be cured, unloading the cured material at the end of a curing cycle, and the like, may be more conveniently performed under the control of a human operator. In many instances a human operator can take into consideration variations in the CCM materials themselves and how they are mechanically handled more easily than can a preprogrammed controller. After the preliminary steps are completed, the human operator can turn over control of the process to a controller, which can control the process for the duration of the curing time. Another benefit of using a controller is that the controller can record and generate a log of the operational parameters that are set as targets, and can record the corresponding actual parameters that are measured during the curing process, so that the precision of the curing process can be increased over time by reprogramming the instructions that control a specific process to cause the actual measured operational parameters to adhere more closely to the values that are set as targets. A well-known example of such improvement in control is the used of proportional-integral-derivative (P-I-D) control when one is trying to set a change in a parameter that finally attains a steady state after a time interval, while attempting to minimize undershoot (too low a value) and overshoot (too high a value) as the desired steady state value is approached.

Figure 28:
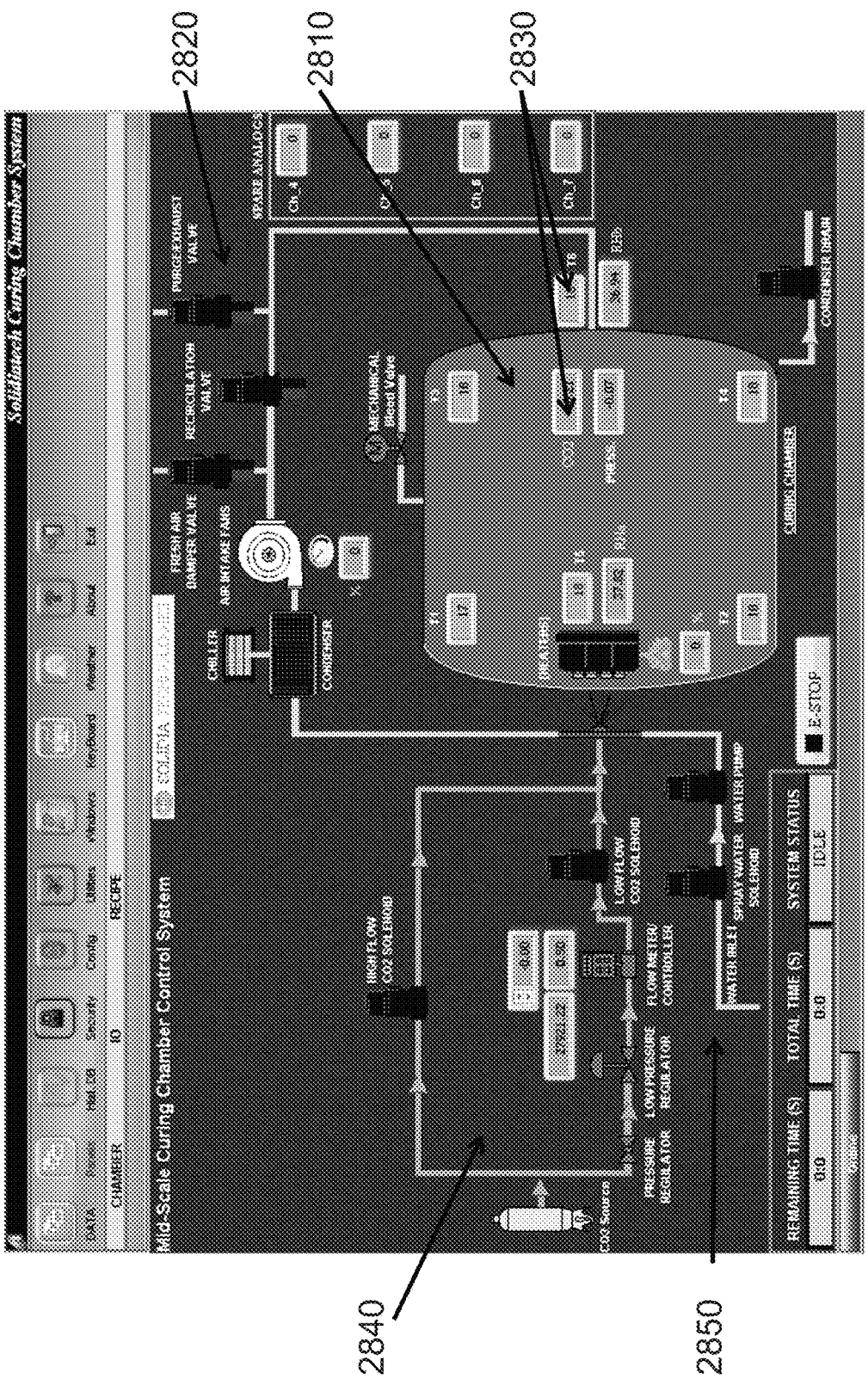
FIG. 28 is a screenshot of a computer based control system for a curing chamber showing a schematic of the system to be controlled.

FIG. 28 is a screenshot of a computer based control system for a curing chamber showing a schematic of the system to be controlled. In FIG. 28 there is shown a schematic of the curing chamber 2810, components of the gas handling system 2820, a plurality of data windows 2830 for the display of process parameters such gas compositions, temperature, pressure, relative humidity, blower speed or flow rates in real time, (e.g., in substantially the then current time as the process proceeds), a schematic of the $CO_2$ source 2840 and associated valves, and a schematic of a source of water/water vapor 2850.

Figure 29:
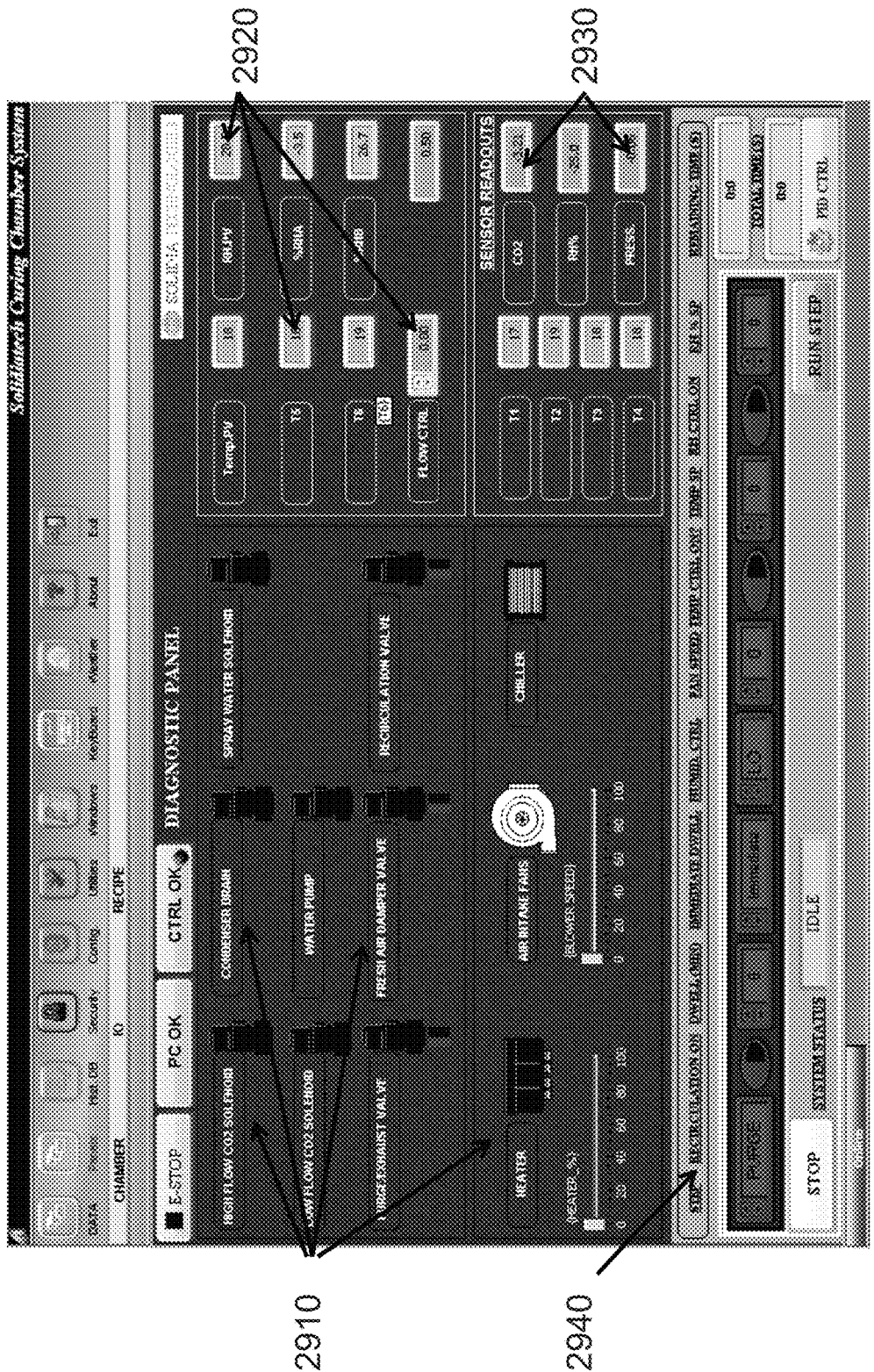
FIG. 29 is a screenshot of a computer based control system for a curing chamber showing a number of components that can be controlled and showing how parameter values that are measured can be displayed.

FIG. 29 is a screenshot of a computer based control system for a curing chamber showing a number of components that can be controlled and showing how parameter values that are measured can be displayed. The screenshot that is illustrated is a diagnostic panel in which are displayed the states 2910 of various components such as blowers, heaters, valves and the like, the desired or programmed values 2920 of various operating parameters, such as temperature, relative humidity, percentage $CO_2$ and the like. The current measured values 2930 provided by various sensors, and a display 2940 of the step that is monitored (here "purge") and some of the parameters that are being controlled. The diagnostic information that is displayed may be different for different steps in the process.

Figure 30:
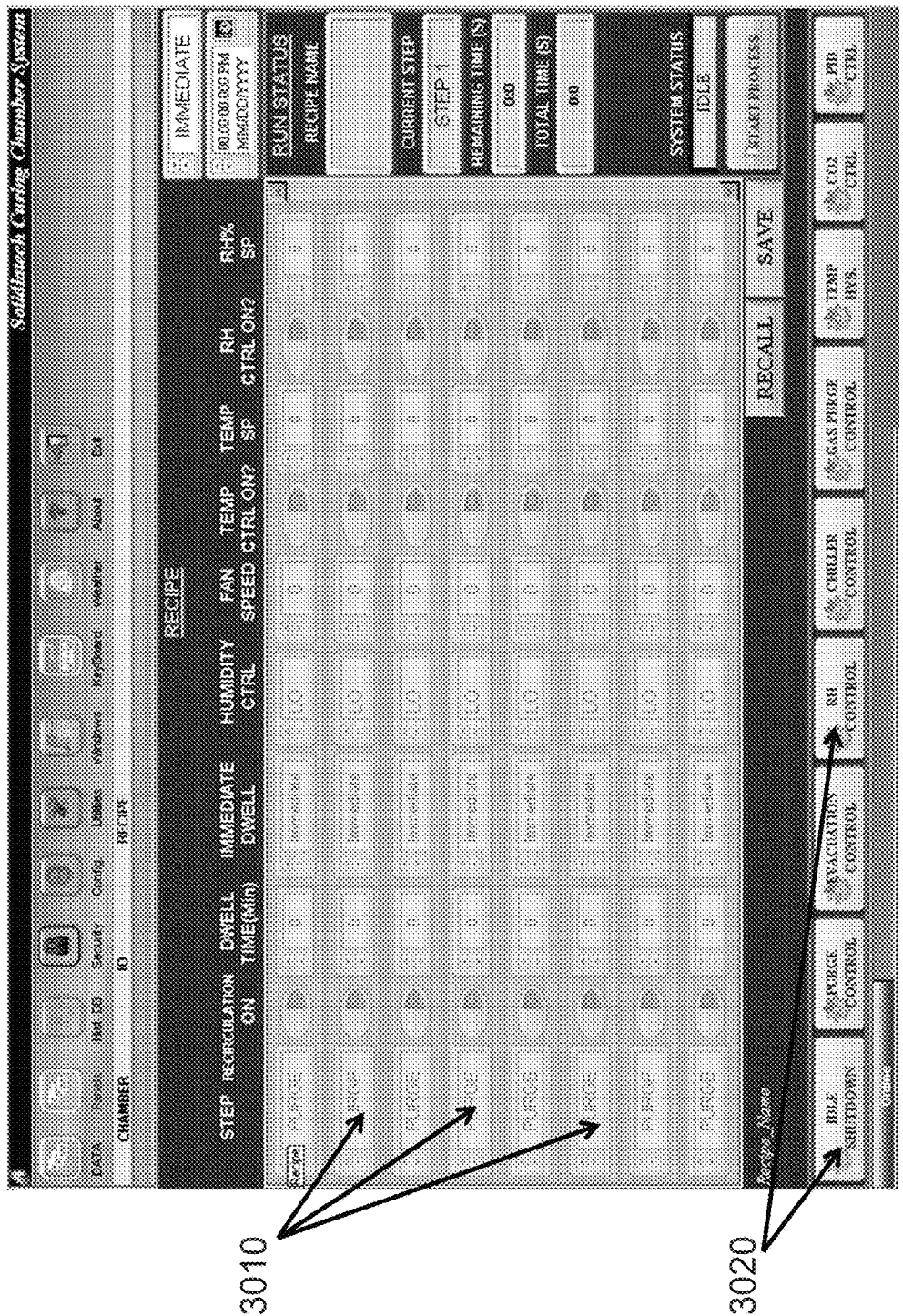
FIG. 30 is a screenshot of a computer based control system for a curing chamber showing a recipe screen in which parameters for various periods or steps in a curing process can be entered by a user or displayed to a user.

FIG. 30 is a screenshot of a computer based control system for a curing chamber showing a recipe screen in which parameters for various periods or steps in a curing process can be entered by a user or displayed to a user. As may be seen, the recipe screen can be used to enter individual steps 3010 with their desired operating parameters. A set of "buttons" 3020 is provided to allow a user to conveniently select different parts of a curing operation, such as control of gas compositions (e.g., a button labeled "$CO_2$ control"), relative humidity conditions (e.g., a button labeled "RH control"), operation of the controller itself (e.g., a button labeled "PID control") and many other parameters. There are also provided buttons to save a recipe to a machine-readable medium or memory, or to recall a previously saved recipe from memory. In some embodiments, the screen itself is a touchscreen. In some embodiments, a pointing device such as a mouse may be used. In some embodiments, a keyboard, a numeric pad, and/or an "on screen" keyboard may be used in enter data or commands.

Figure 31:
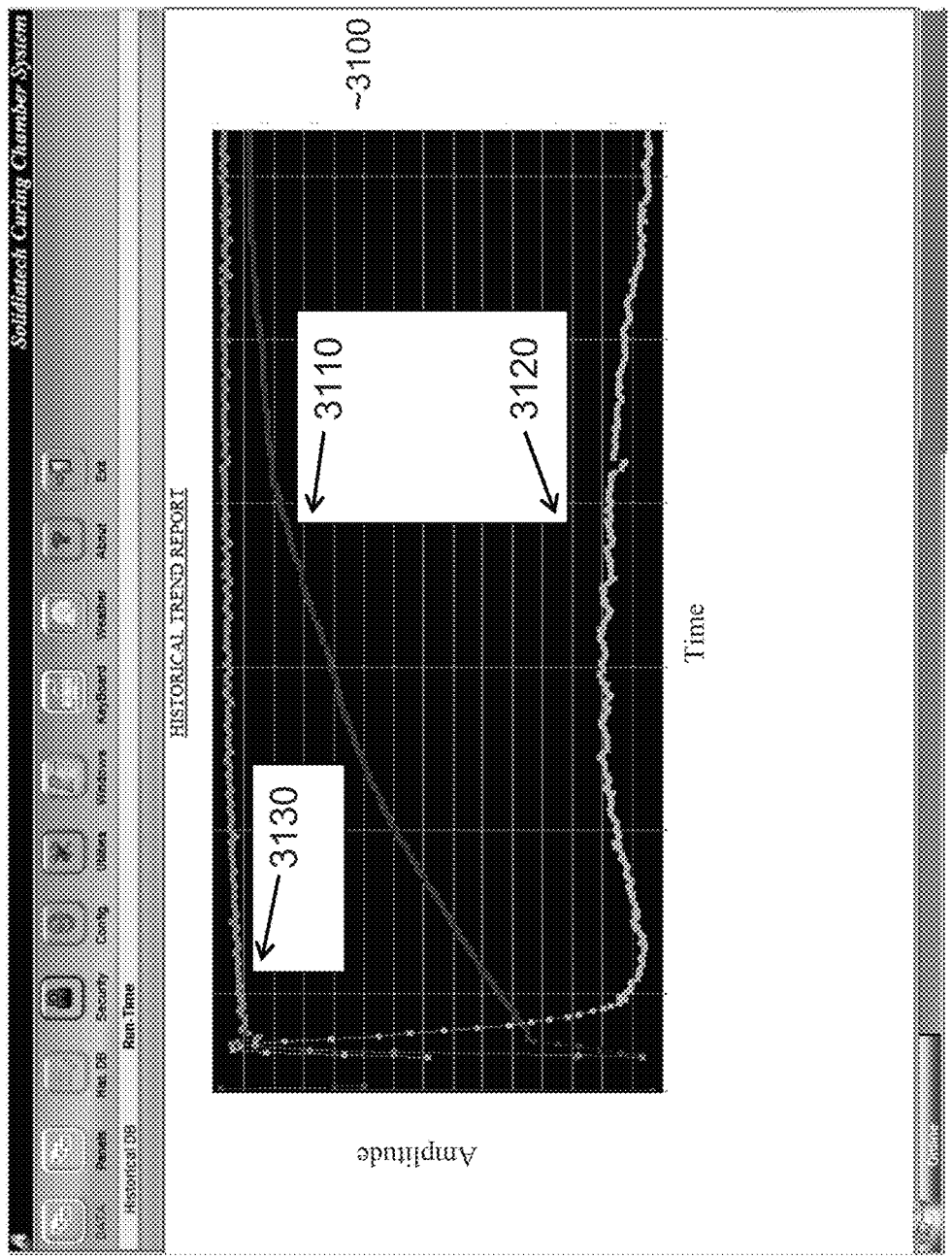
FIG. 31 is a screenshot image of an historical trend report for a curing operation, showing a graph 3100 in which curve 3110 represents total $CO_2$ consumed, curve 3120 represents relative humidity, and curve 3130 represents temperature.

FIG. 31 is a screenshot image of an historical trend report for a curing operation, showing a graph 3100 in which curve 3110 represents total $CO_2$ consumed, curve 3120 represents relative humidity, and curve 3130 represents temperature.

Definitions

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

INCORPORATION BY REFERENCE

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A method of curing a porous concrete product in a $CO_2$ gas, comprising the steps of:
measuring a value of a property of an uncured porous concrete product under a first set of environmental conditions;
supplying said measured value of said property of said uncured porous concrete product to a calculation model that operates on a general purpose programmable computer;
supplying said first set of environmental conditions to said calculation model;
operating said calculation model to generate a calculated water distribution in said uncured porous concrete product under said first set of environmental conditions;
comparing said calculated water distribution in the porous concrete product to a preferred water distribution to obtain a difference between said calculated water distribution in the porous concrete product and said preferred water distribution;

in the event that said difference between said calculated water distribution in the porous concrete product and said preferred water distribution is smaller than a predetermined limit:

performing at least one of recording as a result said first environmental conditions that produce a calculated water distribution in the porous concrete product that differs from the preferred water distribution by less than said predetermined limit, transmitting said result to a data handling system, or displaying said result to a user; and applying said first set of environmental conditions to a curing apparatus;

in the event that said difference between said calculated water distribution in the porous concrete product and said preferred water distribution is not smaller than said predetermined limit:

adjusting one or more of said first set of environmental conditions to generate a subsequent set of adjusted environmental conditions;

supplying said subsequent set of adjusted environmental conditions to the calculation model;

operating said calculation model to generate a subsequent calculated water distribution in the porous concrete product under said subsequent set of adjusted environmental conditions;

comparing said subsequent calculated water distribution in the porous concrete product to said preferred water distribution to obtain a difference between said subsequent calculated water distribution in the porous concrete product and said preferred water distribution;

in the event that said difference between said subsequent calculated water distribution in the porous concrete product and said preferred water distribution is not smaller than said predetermined limit, repeating the steps of adjusting one or more environmental conditions, supplying, operating, and comparing until a difference between a further calculated water distribution in the porous concrete product and said preferred water distribution is smaller than said predetermined limit, and then performing at least one of recording as a result said set of adjusted environmental conditions that produce a calculated water distribution in the porous concrete product that differs from the preferred water distribution by less than said predetermined limit, transmitting said result to a data handling system, or displaying said result to a user; and applying said set of adjusted environmental conditions to a curing apparatus; and in the event that said difference between said subsequent calculated water distribution in the porous concrete product and said preferred water distribution is smaller than said predetermined limit:

performing at least one of recording as a result said set of adjusted environmental conditions that produce a calculated water distribution in the porous concrete product that differs from the preferred water distribution by less than said predetermined limit, transmitting said result to a data handling system, or displaying said result to a user; and applying said set of adjusted environmental conditions to a curing apparatus.

2. The method of curing a porous concrete product in a $CO_2$ gas of claim 1, wherein said property of an uncured porous concrete product is at least one of a water permeability, a porosity, a residual saturation, a sample dimension, a drying side and a critical Relative Humidity.

3. The method of curing a porous concrete product in a $CO_2$ gas of claim 1, wherein said set of preferred environmental conditions includes at least one of a mass transfer coefficient, a relative humidity profile, a temperature profile and a pressure.

4. The method of curing a porous concrete product in a $CO_2$ gas of claim 3, wherein said temperature profile comprises a temperature in the range of 30° C. to 90° C.

5. The method of curing a porous concrete product in a $CO_2$ gas of claim 1, wherein said water distribution in said porous concrete product is a first surface saturation level in the range of 0.05 to 0.8.

6. The method of curing a porous concrete product in a $CO_2$ gas of claim 1, wherein said water distribution in said porous concrete product is a second surface saturation level in the range of 0.05 to 0.8.

* * * * *